US008975043B2

(12) United States Patent
Cox et al.

(10) Patent No.: US 8,975,043 B2
(45) Date of Patent: Mar. 10, 2015

(54) ENZYMATIC DEGRADATION OF LIPID A FATTY ACIDS OF BACTERIAL LPS

(75) Inventors: Andrew Cox, Ottawa (CA); Dhamodharan Neelamegan, Ottawa (CA); Ian Schoenhofen, Ottawa (CA); Frank St. Michael, Ottawa (CA); James Richards, Ottawa (CA)

(73) Assignee: National Research Council of Canada, Winnipeg, Manitoba (CA)

( * ) Notice: Subject to any disclaimer, the term of this patent is extended or adjusted under 35 U.S.C. 154(b) by 351 days.

(21) Appl. No.: 12/093,992

(22) PCT Filed: Nov. 23, 2006

(86) PCT No.: PCT/CA2006/001927
§ 371 (c)(1),
(2), (4) Date: Jul. 31, 2008

(87) PCT Pub. No.: WO2007/059625
PCT Pub. Date: May 31, 2007

(65) Prior Publication Data
US 2008/0317775 A1 Dec. 25, 2008

Related U.S. Application Data

(60) Provisional application No. 60/738,985, filed on Nov. 23, 2005.

(51) Int. Cl.
*C12P 19/26* (2006.01)
*A61K 39/385* (2006.01)
*C12Q 1/34* (2006.01)
*C12N 9/14* (2006.01)
*C12N 5/07* (2010.01)

(52) U.S. Cl.
USPC .......... 435/84; 424/197.11; 435/195; 435/18; 530/350

(58) Field of Classification Search
None
See application file for complete search history.

(56) References Cited

U.S. PATENT DOCUMENTS 4,929,604 A * 5/1990 Munford et al. ............... 514/53

FOREIGN PATENT DOCUMENTS

WO WO01/78787 10/2001
WO WO 03/070282 8/2003

OTHER PUBLICATIONS

Verret et al. The Journal of Biological Chemistry. vol. 257, p. 10228-10234, 1982.*
Bork (Genome Research, 2000,10:398-400).*
Lazar et al. (Molecular and Cellular Biology, 1988, 8:1247-1252).*
Bowie et al (Science, 1990, 257:1306-1310).*
Burgess et al. The Journal of Cell Biology, vol. 111, Nov. 1990 2129-2138.*
Sharma et al (Rev Environ Sci Biotechnol (2009) 8:343-366).*
Pace et al (Genome Biology 2001, 2(1): reviews 0001.1-00001.9).*
Whisstock et al (Quaterly Reviews of Biophysichs 36, 3 (2003), pp. 307-340).*
Verret, C.R., "Lipases Specifically Degrading Lipopolysaccharide: Fatty Acyl Amidases from *Dictyostelium discoideum*.", Reviews of Infectious Diseases, 1984, vol. 6(4), pp. 452-454, ISSN 0604-0007, entire document.
Sutherland, P.J. et al., *Dictyostelium discoideum* Fatty-acyl Amidase II Has Deacylase Activity on Rhizobium Nodulation Factors, J.B.C. 1998, vol. 273(8), pp. 4459-4464, ISSN 0021-9258, entire document.
TrEMBL Database, Accession No. Q54L63, May 24, 2005. http://www.ncbi.nlm.nih.gov/entrez/viewerfcgi?db=protein&val=74853254.
TrEMBL Database, Accession No. Q8MMR8, Oct. 1, 2002 http://www.ncbi.nlm.nih.gov/entrez/viewerfcgi?db=protein&val=74865798.

* cited by examiner

*Primary Examiner* — Oluwatosin Ogunbiyi
(74) *Attorney, Agent, or Firm* — Michael R. Williams; Ade & Comapny Inc.

(57) ABSTRACT

Novel enzymes, processes and antigenic structures useful in producing vaccines and compounds useful in combating gram-negative bacteria are described. Enzymes were isolated from the slime mold *Dictyostelium discoideum* and used to specifically degrade lipopolysaccharide (LPS). Enzymatic degradation permits residues of the LPS molecule, including immunogenic epitopes of the core oligosaccharide portion of the LPS, to remain unmodified during this enzymatic removal of fatty acids from the lipid A region of the LPS molecule.

3 Claims, 33 Drawing Sheets

▲ = fatty acid amidase I (FAAI)
■ = fatty acid amidase II (FAAII)

Fig. 5a. *Dd* 1 (550 aa with MW 61,155 Da on Chromosome 4)

MNRLTNISKIRKSLIDGKLKVNDLVLNKIKEINKVSPNHLNTFISLQDEKSLGKQIK
ESQERYDNGTNKRLDGIPIGVKDNFSSKNFKTTCGSKILENYIPSFDSTVVKLLKE
EGAIIIGKTNMDEFSMGSSSTSGHFGKVINPWSKPNNNNNNDNDNNNNGEVLYV
AGGSSGGSAAAVASNYCVASIGSDTGGSIRQPSSYCGVVGFKPSYGLISRFGLVA
YASSLDTPGVLTNNVEDAAELLDILIKKDQENDSTSIEFINNNQNQNQNNGEKRNI
LDEFNEKLKNKNIKDLVFGIPKDYLVKELDTDILNLWKEVVEEIEKRGGKVVSVS
LPHTRYALPAYYLLATSEASSNLSRFDGVRYGYRFEEEKDENKVDNDNDDDDD
VDENKIGMGLKDMYTKTRTNGFGEEVKKRIILGTMALSRSSYDNFYTKAQKIRR
LVSDDFKNVFQGENKVDILITPTAPSPAFKQNEKMDPIEVYVNDIMTIPSNLAGLP
ACSIPLKLSNSNLPISVQLISNRLTDDNLLFAAHTIMNFDCYKDFTSLTPNYLK

Fig. 5b. *Dd* 2 (637 aa with MW 70,282 Da on Chromosome 2)

MTSSSLSKSSSTSSTSSKNEEKGEKKIYDLISLEVPRLQGLLLRSTLFLCENHYLKN
SFLSSLYTKNKMPLISQFNLNLSPTFYPIVDISNHQQQQQNKSEFTFKKYLATDML
HDKDLIKYLQSKNLEINSQSSSSSSSNNQSLINNIPENSIINYYNLYMTGKITPNEIA
NFFIECKNHSDEQSPPLKAFIKILEDDIKSQAMASAERWKSGSPLSLIDGVPISLKD
EIDQIGYHTTCGTTFLEKVFPNVKTEDSGVAKMLRQQGAILVGKNNMHEIGISTL
GYNTHFGFTRNPYNLNHYPGGSSSGSASSVSAGLNPLSIGCDGGGSIRVPASLCG
VVGLKPTFARVSHGGIFDLCWSVGHVGPIGSSVIDTAIGYACIAGSDSADHQSVL
AEQYGGKPTVPMFTEIPLIQPLKGLKIGVFYDWINDCNIEFKDSTYKCIEILKEQG
AEIIEIEISNLLVTRLSQGAIILSEMNSSMKRFKNYSNELQYDSRISLSIGNILPTSDY
LQANKVRTFCIEQFTEIFKGVDLIVTPTNAIAAPEIEKSVLSMGESNFGSVGELMK
YVFIGNITGIPGITVPVGLTKDKNLPIGFQIMAKWWQEDLLLYTSYVLEKNIDFKG
KPQYYNCPLTNCTNPNN

ATGTATAGATTCTAAATGTCAATTATATGGTATTGAACGTAGTGAATATATTACTTGTAT
CGATTATTATAATTGTCCAGGTCCAAATACATGTGCTTCATTAGGTTTTGATAATGGAAA
TTACATTTCAAATGTGTGCCTTTAAAACCATTAAAAAGTGATTGTAAAACTCAATCAGA
ATGTTTCATTGGTGGTATATGTTCAAGTGAAAATAAATGTATTTCAAGATATTCAAAGAA
ACTAAATGAAAATTGTTTATATAATAGTGAATGTGATTTTGGATTAAAAGTAAGTAAAAA
AAAAAAAAAAAAAAAAAAAAAAAAAAAAAAAAAAAAAAAAAAAAAAAAAAAAAAAAAA
AAAAAATTAATTTAACAAATAATAACTCCTATTTTTACCAATACAATAAGTGTGAAACTA
CAATTTATCATTATTTTCCAAATGGTACATTTAAAAATTTTGAAGAAATTAATAAATGTG
TACCATTGATCTATTCAAAAACAACAAATTGTTTAGATGAAGGTTGTCAAGAATATGAAT
TTTGTAATGGTGCAACAAATAAATGTTATCCTAAAAAGAAATACACAAATGATTGTAAAA
AAGCAGAAAAAGAAAGAGATTCATGCTACATTTCAAATAACTGCTTCTTTTCAAATGAAC
AATATGATTTACTATCTTCTGATTCTCCATTTTCAAATGAAAATTCTTGTCAAATGAAAC
ATTGTAAATGTCAAACAATCAATTATTTTAACCAATGTCAAAATACATATACATTTTGTC
AATAAAACCTTTGATAATAAATATATATTAAAATTTCATTTTTACCTTATTATAATTTTT
TTTTTTTTTTCAATTCTCCCTTAATATCACTTTTTTTTAAAAAAAAAAAAAAAAAAAAA
AAAAATCAAAAAACTCGTTTAAACGACTTTTTTTAATTTTTATTTTTTTATTTTTATT
TTTTATTTTTAATTAAAAAAATCATTGATGATTAAAAACG<u>ATGAATAGATTAACAAATAT</u>
<u>ATCAAAAATTAGAAAATC</u>ATTAATAGATGGAAAATTAAAAGTGAATGATTTAGTTTTAAA
TAAAATCAAAGAGATTAATAAAGTTTCACCAAATCATTTAAATACATTTATTTCACTTCA
AGATGAGAAATCATTAGGGAAACAAATTAAAGAGAGTCAAGAGAGATATGATAATGGTAC
AAATAAAAGATTAGATGGTATACCAATTGGTGTAAAAGATAATTTCTCAAGTAAAAATTT
TAAAACAACTTGTGGTTCAAAGATTTTAGAGAATTATATACCAAGTTTTGATTCAACTGT
TGTTAAATTATTAAAAGAGGAAGGTGCAATAATTATTGGTAAAACTAATATGGATGAATT
TTCAATGGGTTCATCTTCAACTTCTGGTCATTTTGGTAAAGTAATTAATCCATGGAGTAA
ACCAAATAATAATAACAATGATAATGATAATAATAATAATGGAGAGGTTTTATATGT
TGCAGGTGGTTCATCAGGTGGTTCGGCAGCAGCAGTTGCTTCAAATTATTGTGTTGCATC
AATTGGATCAGATACAGGTGGTTCAATTAGACAACCATCATCATATTGTGGTGTTGTTGG
TTTTAAACCATCCTATGGTTTAATATCACGTTTTGGTTTAGTTGCATATGCTTCATCATT
AGATACACCTGGTGTTTTAACTAATAATGTTGAAGATGCTGCTGAATTATTAGATATTTT
AATTAAAAAAGATCAAGAAAATGATTCAACTTCAATTGAATTTATAAATAATAATCAAAA
TCAAAATCAAAATAATGGTGAAAAAAGGAATATTTTAGATGAATTTAATGAAAAATTAAA
AAATAAAAATATAAAAGATTTAGTATTTGGTATACCAAAAGATTATTTAGTTAAAGAATT
AGATACAGATATACTTAACCTTTGGAAAGAAGTTGTTGAAGAAATTGAAAAAAGAGGTGG
TAAAGTTGTATCAGTTAGTTTACCACATACTCGTTATGCATTACCAGCTTATTATTTATT
AGCAACATCTGAAGCAAGTTCAAACCTTTCAAGATTTGATGGTGTTAGATATGGTTATAG
ATTTGAAGAAGAAAAGATGAAAATAAAGTAGATAATGATAATGATGATGATGATGATGT
TGATGAAAATAAAATTGGTATGGGATTAAAAGATATGTATACAAAAACTAGAACAAATGG
TTTTGGCGAAGAAGTTAAAAAAAGAATTATACTTGGTACAATGGCATTATCAAGATCATC
ATATGATAATTTCTATACAAAAGCTCAAAAGATTAGAAGATTAGTATCAGATGATTTTAA
AAATGTTTTCCAAGGTGAAAATAAAGTAGATATTTTAATAACACCAACTGCACCATCTCC
AGCATTTAAACAAAATGAAAAAATGGATCCAATCGAAGTTTATGTAAATGATATTATGAC
AATACCTTCAAATTTAGCAGGTTTACCAGCATGTTCAATTCCTTTAAAACTTTCAAATTC
AAATTTACCAATTTCAGTTCAACTAATTTCAAATCGTTTAACTGATGATAATTTATTATT
TGCAGCTCATACAATTATGAATTTTGATTGTTACAAA<u>GATTTTACATCACTTACACCAAA</u>
<u>TTATTTAAAA<b>TAA</b></u>TAAAATAAAAATTATAAACACTATAGTGTTTGTTTATTTAAAAATTA
AATCTTTTATATAATTTGTTTTATATTTTATCCACCATTTATATTTAAATAAAATTAAAA
TTATTGTAATAATAATTATAACACCAATTATTGAACAAACTATTAAAATTATTAAATCAT
TTTTTGATAAATTATTTGATTGAAATGATTGTGAATAATTGAATGATTTTGAATTCGATG
ATGATAATAATGATGATTTACTACAAACTGTAGTATCACTATCAGAATTACCACCTAATA
AAAATTGAAAATTTGGATCAATTATTGCTTTCTTTTTAAAATTGGGAATATTAATTGCAA
CTTGTATTGATATTTCTTGAGAATTTATACTTTTAACCAACGAATTTGGAATTATTGAAT
TTGATAATAAAATTTTTTATCATCAATAATACCTTTCTTTATAAATTCACCAACCATTG
AAATTTCATTAACCCTTAATACAATCCATGATAAATTTGTTTCATTTAAATTTCTATATC
CAAATGAATTTGAAATACATGTCGTTTTATCATCGTCATTATATTTTAATGTTGAATTAA
ATATAATTTGTAATGTATTTAATGGTGAGCTAAATTGATAATTTAAAATTTCAATTGAAA

FIG 7 cont...

```
ATTTTAATGTATTTGGTTTAACACTTATTGATTCACCAGCAAATTCTAAAATTGTTGATA
AATTTGATTGATTTTGAGGGAATTTTGAAATTATAATTTTAATTTCACTATAACCATTTT
CAGTTGGGAATTTATTTGAATACATTATTGATGTTGCATTATATTGATTGAATGATGAAT
TTTCATAATTTTTAAAAACTTTCCATGGTAATTTTGAAAAATCAAATTCTTTAACAATTT
CATTTGAAAAACCAACTTCACAAACTTTAAAAAATGATATATCAGCATAACCACCTCCAC
AATTATTATTATTATTATTATTATCTGATTTAATCCATTGATAAGTTGATGGT
```

Fig. 8.

```
GTAGAGAACAAGAAACAAACAAAACAACAAATCCAAATAACTCTAAAAAATTAAAAAATT
TCAAAAATAATAATCATTATTTTATTGTGTATATATATAGAAAAAAAAAAAAAAAAAAAA
AAAAAAAAAAAAAATAAACTACCAACCTTTTTATTTTTTTTTTTTTTCCAAATTTTTT
TTTTTTTTCTTAAAATTACTAAAACATTCTCTATTACTTAACATATTAATTAATCAATAT
TTTTAAAAAAAGTTAAAATGTTATTTTTATTAAAATAGATTAATAATTGAAGGAAAAAA
AAAAAAACCATAAAATAAAATAAAAATGATAGATCTAAATAAAATAAACCTTTCAAAAAA
ACTTTATTTTTTGAAATTAATTAAACACAAATTTCTTCCAAAATAAATAACAATTTTATA
TTTTTTGACAACATTAATTAAAAAGGAAATAAATAGTTTTTTATTTTTATTATTTTTTT
TTTTTTAGGGCAAAGATTAATAATAATTTTCCAATTTTTTCAAACCTCCCAATTTTTACC
ACCACACATTCGAACCAAAATTTTCACATCTATAATTTTTATCGTCATTTTTTATTATT
TTTTTTTTTATTATTATTAAAATGTTTGGTTTTGAATTTAAACACATAAATCTTGATT
TATGTGTTTTTTTTTTTTTTTTTTTAATTTTTAAAATTTAATTTATTTTTTATTTTT
TTTTTATTTTATTTTAATTTTTTAATTTTTAATTTTTAAATTTTTATTTTTAATTTT
TTTTTTTTTTTTTTTTTTTGAATCTTCCCAAGTTTACTTGTATGCATTTTAAATATT
TAATTAAATTAGCCCACACACAAAAATAATTCTTAAAAAAAAACCCTTTTTTTTTTTTT
TTTTTTTTTTCTTTCCATTTTAGGTTAAATAATTTATTATTATTTTTTTTTTAATAA
TTAAAAACTTCCTTTATTTTTTTTCTCTATCAATAGGAAATGACATCTTCTTCATTAAG
TAAAAGTAGTAGTACAAGTAGTACAAGTAGCAAGAATGAAGAAAAAGGTGAAAAGAAAAT
TTATGATTTAATATCATTAGAAGTTCCAAGATTACAAGGACTTTTATTAAGATCAACTTT
ATTTTTATGCGAAAACCATTATTTAAAGTAAGTATTTTTATTTTTATTATTTTTTTTTT
TTTTTATATGTGTGGTTAGTTTTTTGATTTTTAAATAATTATAAAAAAAAAAAAAAATA
AAAAAAAAACCAATTGTCTTGTCACTTTCACACAGTCACACACTCAATTATTTTCGATTA
ATTGTAATCTAATCTTTTTTTTTTTTTTTTTAAATTCTAATTTTATAAAAAAAGGAAT
TCATTTTATCGTCATTATATACAAAAAATAAAATGCCATTAATTTCACAATTTAATTTA
AATTTATCACCAACCTTTTATCCAATTGTTGATATTTCAAATCATCAACAACAACAACAA
AATAAATCTGAATTTACATTTAAAAAATATTTAGCAACTGATATGTTGCATGATAAAGAT
TTAATTAAATATCTTCAAAGTAAAAATTTAGAAATAAATAGTCAATCATCATCATCATCA
TCATCAAATAATCAATCATTAATTAATAATATACCAGAGAATTCAATTATAAATTATTAT
AATTTATATATGACTGGAAAGATAACACCAAATGAAATTGCAAATTTTTTTATTGAATGT
AAAAATCACTCTGATGAACAATCACCACCATTGAAAGCATTTATAAAGATATTGGAGGAT
GATATTAAATCTCAAGCAATGGCAAGTGCTGAACGTTGGAAATCCGGTTCACCTTTGTCA
TTGATTGATGGTGTACCAATCTCATTAAAAGATGAAATAGACCAAATTGGATATCATACC
ACTTGTGGTACAACCTTTTTGGAGAAAGTATTTCCAAATGTTAAAACTGAAGATTCTGGT
GTAGCCAAAATGTTACGTCAACAAGGTGCAATTTTAGTTGGAAAGAATAATATGCACGAA
ATTGGTATCTCAACACTTGGTTATAATACTCATTTTGGGTTCACTAGAAATCCATATAAT
CTCAATCATTATCCAGGTGGTAGTTCTTCAGGAAGTGCTTCTTCAGTATCGGCTGGTTTA
AATCCATTAAGTATTGGTTGTGATGGTGGTGGTTCAATTAGAGTACCTGCTTCATTATGT
GGTGTCGTTGGTTTAAAACCAACTTTTGCAAGAGTTTCTCATGGTGGTATTTTTGATTTA
TGTTGGTCAGTTGGTCATGTTGGTCCAATTGGTTCGTCAGTAATTGATACTGCAATTGGT
TATGCTTGTATTGCTGGTTCTGACTCTGCCGATCATCAATCTGTTTTAGCTGAACAATAT
GGCGGTAAACCAACCGTTCCAATGTTTACTGAAATTCCATTAATTCAACCATTAAAAGGT
TTAAAAATTGGTGTTTTTTATGATTGGATTAATGATTGTAATATAGAATTTAAAGATTCA
```

FIG 8 cont...

ACTT**A*TA*GTAAGTAAAAAAAAAAAAAAAAAAAAAACAATTAAAAATTAATAATAATATTAA
TAATTCATTACTTTGATTAATTATTAG*AATG**TATTGAAATTTTAAAAGAACAAGGAGCTG
AAATTATAGAAATAGAAATTTCAAATTTATTAGTAACTAGATTATCACAAGGCGCAATTA
TTTTATCAGAAATGAATTCATCTATGAAA*AGAG**TAATTATTTAATTTATTTAATTATTTT
TTATTAATTTAATTAAATTTTATTAATATAATTTTTTTTTTTTTTTTTTTTTACATTTA
AAAAAATAG*TTTAAAAATTATAGTAATGAATTACAATATGATAGTAGAATTTCATTATCA
ATTGGTAATATATTACCAACTTCAGATTATCTTCAAGCAAATAAAGTTAGAACTTTTTGT
ATTGAACAATTTACTGAAATTTTTAAAGGAGTTGATTTAATTGTAACACCAACTAATGCA
ATAGCTGCACCTGAAATTGAAAAAAGTGTTTTGTCTATGGGAGAATCAAATTTTGGATCA
GTAGGTGAATTAATGAAATATGTTTTTATTGGAAATATTACTGGTATCCCTGGCATAACT
GTTCCAGTGGGTCTAACAAAAGATAAAAACTTACCAATTGGTTTTCAAATTATGGCAAAG
TGGTGGCAAGAAGATTTACTTTTATACACTTCTTATGTTTTAGAAAAAAATATTGACTTT
AAAGGAAAACCACAATATTATAATTGTC<u>CTTTAACAAATTGCACAAACCCAAATAACTAA</u>
TATTTAAAATAAAATAATTTATAAGATATATTTTTTTTATTGTTTATTATTTTTTTTTT
TAAAGGTGAGAATTTTAAAATGTAAAGAAGTTATTCCTTTTAATTTTAATTTTCAAATAA
GGAATTTTAATTTAAAAATAAAGTGTGGCTTTTATTTTTGTTTATAAATAAATTAAAAAA
ATAAATCAGTTCCACCAATTCAATTAATAAATTACAAAGGAGAAACTATTTGTAAGTATT
GATTCTGGAATAATATACTTTTCAAGTTAATTTCTTAATCATTTGTTTTTTTCAATTTC
ATTTTAGAAGACTAGGATTTTTTTTTTTTATAAATAAACTATTGTAGTATACAATTAGT
ATGTTATTTTTATTTATTTATTTTAGGTTTTTTACTTTTTGAGAATTTAAAATGGTATGT
TATTTTAGATTAGGTAATTAATAATTAATTGGTGGTGTAATTGTTGGAATTAGAGGACTA
GGAATCGAACCTTTTTTATATTTTTTTATATTTTTTTACTAGGAATCGAACCTACGAT
TTTGCTTTTCTCCCCATAAAAATTCACCCATTGTGGGTCTCGATCCCACGACCTGCAGCT
TAGAAGGCTGCCGCAATTCCAACTTTGCTAAACGGGCTTTGATGAATTCTTTGTAATAAA
GCTTGTTAGCTTTATAAATATATAGGAGATCGAAAAAAAACAAACAACAACAACAATCTC
TTTTTTTGATTATTTCATTTTTCATATAAAAAAGACTTAAAAAACAAATAAATAAATAAA
TAAACTATCTTAAAAAGCCATCTTTTTACTTTATTGTAATTTATTATTTGTTTCGTTTTG
AGAATTTTGCGTAGCAAAATTTTCAAAAAAAAGCAAAAAATAATCAGATCGAAAAAAAAC
AAACAACAACAACAATCTCTTTTTTTTGATTATTTCATTTTTCATATAAAAAAGACTTAAA
AAAAAAAAAAAAAAAAAAAAAAAAAAAAAAAAAAAAA

Fig. 22
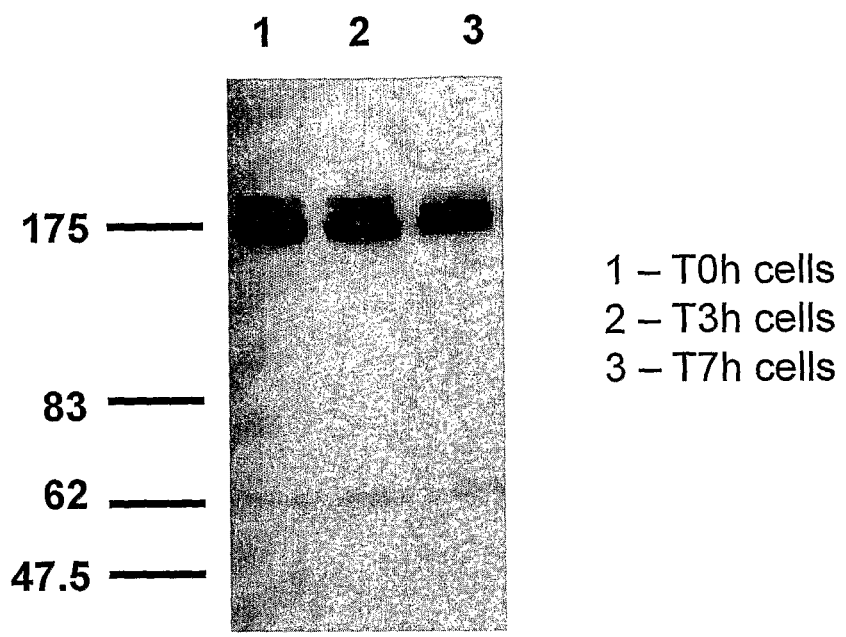
1 – T0h cells
2 – T3h cells
3 – T7h cells
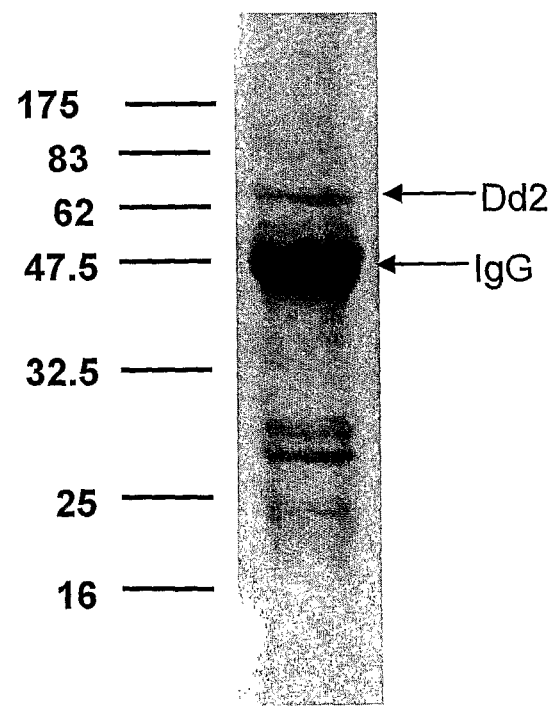
Fig. 23.

alkP treatment

L3 galE O-deac, Dicty, alkP

$646.3^{3-} = 969.8^{2-} = 1941.6$

2GlcN, 1FA, 1P, 2Kdo, 2Hep, GlcNAc, Glc, PEtn = 1941.5

Lanes:

1: CRM

2: activated CRM

3: purified L3*galE*-conj; Dicty

Fig. 49.

% survival vs % Rabbit serum

- ⋯□⋯ R2 pre MC58 galE
- ■ R2V MC58 galE
- ⋯△⋯ R2 pre-MC58
- ▲ R2V MC58

ENZYMATIC DEGRADATION OF LIPID A FATTY ACIDS OF BACTERIAL LPS

PRIOR APPLICATION INFORMATION

This application is a national phase application of International Patent Application No. PCT/CA2006/001927, filed Nov. 23, 2006, which claims the benefit of U.S. Provisional Patent Application 60/738,985, filed Nov. 23, 2005.

BACKGROUND OF THE INVENTION

Gram-negative bacteria can cause diseases of significant public health and economic concern in humans and other animals. Vaccine strategies are being pursued to combat these infections. These strategies are based on the identification of conserved, immunogenic cell surface components; however, the detection of conserved molecules that would confer protection against the vast majority of strains from a single species has proven problematic.

The exterior surface of the outer membrane of all Gram-negative bacteria contains an amphiphillic carbohydrate molecule termed lipopolysaccharide (LPS) that by virtue of its surface location can be considered as a candidate vaccine antigen. As its name suggests this molecule contains a lipid region that anchors the molecule in the outer membrane, by virtue of both ester (O—) linked and amide (N—) linked fatty acids. The lipid A region and specifically the fatty acids are responsible for the endotoxic activity of the Gram-negative bacterium and consists in most species of a disaccharide of glucosamine sugars that are phosphorylated and the ester and amide linked fatty acids as shown in FIGS. 1 and 2.

The core oligosaccharide can be arbitrarily divided into an outer and inner core and is connected to the lipid A region via one or more ketose sugar(s), 2-keto-3-deoxy-octulosonic acid (Kdo). An O-antigenic polymeric repeating unit (O-antigen) can be present or absent beyond the core oligosaccharide of the LPS molecule. The O-antigen is a variable moiety between strains of the same species and is often the antigen responsible for the serotyping schemes adopted to classify a species. Due to its variable nature within most species the O-antigen is not a good vaccine candidate as antibodies directed to one O-antigen will be serotype specific, and not offer protection to other serotypes of the same strain. Similarly the outer core region can be somewhat variable within a species and is also therefore not a good vaccine candidate. However what is arbitrarily termed the inner core oligosaccharide has been found to be conserved within several species, and is the vaccine antigen of choice in this application. Conserved regions of LPS molecules have been identified in the core oligosaccharide of several species, and examples of core oligosaccharide structures are detailed in FIG. 3 below for LPS from the species *Neisseria meningitidis, Haemophilus influenzae* and *Mannheimia haemolytica*. For the purposes of this discussion, but not restricted to just these structures, the inner core region for *Neisseria meningitidis, Haemophilus influenzae* and *Mannheimia haemolytica* linked to the lipid A region are illustrated in FIGS. 3b-d. However the technology described here would be equally applicable to the other LPS carbohydrate antigens, outer core oligosaccharide and O-antigen.

The endotoxicity of the lipid A region is due to the fatty acid residues. Removal of the ester-linked fatty acids leaves an O-deacylated LPS species that is no longer endotoxic. Removal of all fatty acids i.e. both the amide and ester-linked fatty acids can be performed chemically, but involves harsh conditions which can effect other regions of the LPS molecule. Even the mild chemical conditions employed to effect O-deacylation can effect ester-linked residues elsewhere in the LPS.

LPS based vaccines generally require the removal of fatty acids from the lipid A region of the molecule to reduce the endotoxicity. Preferably, this detoxification step does not modify the carbohydrate epitopes on the LPS molecule, however commonly available techniques do not permit this.

Current methods employed are to chemically O-deacylate LPS producing an O-deacylated LPS molecule (LPS-OH) which can be used either directly or following further modification to conjugate to a suitable protein carrier to produce a glycoconjugate vaccine candidate. Removal of the remaining N-linked fatty acids from LPS-OH would greatly improve conjugation strategies, as this would create a completely water-soluble molecule amenable to all subsequent manipulations. However, chemical methods currently employed to de-N-acylate LPS molecules also modify some residues in the inner core, thus altering the structure of potentially immunogenic epitopes on the LPS molecule. For example the phosphoethanolamine (PEtn) residue of the inner core oligosaccharide of *Neisseria meningitidis* LPS (FIG. 3ab), a known immunogenic moiety, is sensitive to the chemical conditions required to remove the N-linked fatty acids, thus modifying a conserved residue in the inner core LPS and creating a molecule which is no longer representative of the native LPS structure.

SUMMARY OF THE INVENTION

According to a first aspect of the invention, there is provided a method of preparing a vaccine comprising:
separating lipopolysaccharide from a bacterium of interest;
de-esterfying the lipopolysaccharide;
removing at least one N-linked fatty acid from the lipopolysaccharide with an isolated amidase activity; and
conjugating the modified lipopolysaccharide to a suitable carrier molecule.

According to a second aspect of the invention, there is provided a method of recovering a modified lipopolysaccharide from a bacterium of interest comprising:
separating lipopolysaccharide from the bacterium of interest;
de-esterfying the lipopolysaccharide;
removing at least one N-linked fatty acid from the lipopolysaccharide with an isolated amidase activity; and
recovering the modified LPS.

According to a third aspect of the invention, there is provided an isolated or purified mono-N-acylated-de-O-acylated lipopolysaccharide (LPS) molecule or de-N-acylated-de-O-acylated LPS molecule from a bacterium of interest conjugated to a carrier protein.

According to a fourth aspect of the invention, there is provided use of the conjugate as described above for the immunization of individuals having or suspected of having or at risk of developing an infection from the bacterium of interest.

According to a fifth aspect of the invention, there is provided use of the conjugate as described above in the manufacture of a medicament for the immunization of individuals having or suspected of having or at risk of developing an infection from the bacterium of interest.

BRIEF DESCRIPTION OF THE DRAWINGS

FIG. 5a is the Dd1 amino acid sequence.

FIG. 5b is the Dd2 amino acid sequence.

FIG. 6 is a fatty acid amidase consensus sequence alignment. FAAH sequence comparison among human (FAAHI and FAAHII), Rat, *Dictyostelium* (DD1 and DD2) and *Arabidopsis*. *Dictyostelium* amidases (DD1 and DD2) share the amidase signature (underlined) and the conserved motif, GGSS(G/A/S)G (boxed) in the predicted amidase signature with other members.

FIG. 7 is Dd1: one exon with start codons underlined, stop codons in bold, indicators of beginning and end of exons in bold italics and primers double-underlined.

FIG. 8 Dd2: 4 exons and 3 introns, with start codons underlined, stop codons in bold, indicators of beginning and end of exons in bold italics and primers double-underlined.

FIG. 22 is a Western blot analysis of in vivo expression of Dd2 in *Dictyostelium* cells: The polyclonal antiserum recognises an in vivo protein at 70 kDa, and also recognises a 175 kDa protein which may be modified Dd2, Dd1 or a non-specific protein.

FIG. 23 is a SDS-PAGE following immunoprecipitation of in vivo Dd2 protein using polyclonal antisera NRC-Dd2, stained with Coomassie blue.

FIG. 49 is a bactericidal assay using pre- and post-immune sera from vaccinated rabbit #2 with *Neisseria meningitidis* strains MC58 galE and MC58.

DESCRIPTION OF THE PREFERRED EMBODIMENTS

Figure 1:
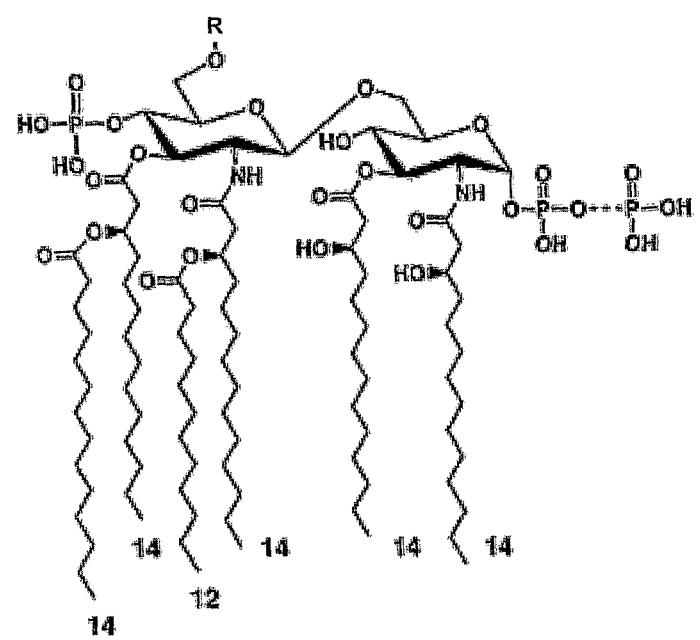
FIG. 1 is a schematic representation of the lipid A region of *Escherichia coli* LPS molecule where R is the core oligosaccharide-O-antigen region of the LPS molecule, and the numbers at the bottom of the figure refer to the chain length of the fatty acid molecules. The phosphorylation of the lipid A can also vary, e.g., P, P-P or P-PEtn.
Figure 2:
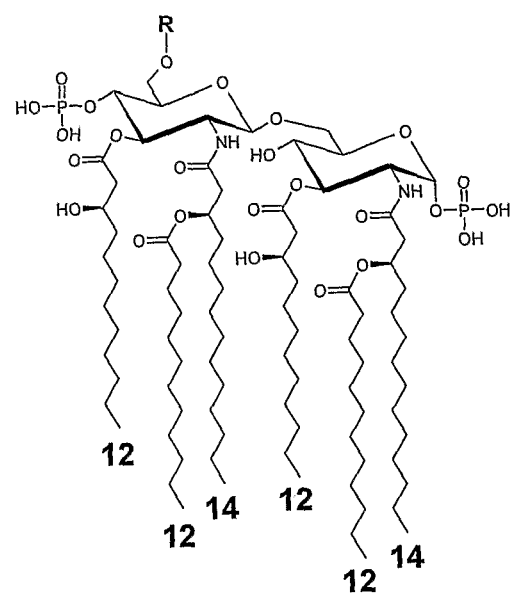
FIG. 2 is a schematic representation of the lipid A region of the *Neisseria meningitidis* LPS molecule, where R is the core oligosaccharide region of the LPS molecule, and the numbers at the bottom of the figure refer to the chain length of the fatty acid molecules. The phosphorylation of the lipid A can also vary, e.g. P, P-P or P-PEtn.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

There is disclosed herein novel enzymes, processes and antigenic structures useful in producing vaccines and compounds useful in combating gram-negative bacteria. Enzymes were isolated from the slime mould *Dictyostelium discoideum* and used to specifically degrade lipopolysaccharide (LPS). Enzymatic degradation permits residues of the LPS molecule, including immunogenic epitopes of the core oligosaccharide portion of the LPS, to remain unmodified during this enzymatic removal of fatty acids from the lipid A region of the LPS molecule.

Also disclosed are strategies employed to obtain and purify desired enzymatic activities either directly from *Dictyostelium discoideum* or following cloning and expression in an appropriate expression system, and uses of enzymes isolated in this way.

According to an aspect of the invention there is provided a method of preparing a vaccine comprising:

separating the lipopolysaccharide from a bacterium of interest;

de-esterfying the lipopolysaccharide;

removing at least one N-linked fatty acid from the lipopolysaccharide with an isolated amidase activity; and conjugating the modified lipopolysaccharide to a suitable carrier molecule.

The bacterium is preferably a gram-negative bacterium. As will be appreciated by one of skill in the art, the bacterium may not necessarily be a known or positively identified bacterium but need only be sufficiently purified or isolated so that the lipopolysaccharide can be recovered therefrom.

As used herein, 'purified' does not require absolute purity, but only that the material has been purified, for example, by 2 fold, by 5 fold, by 10 fold or more.

As used herein, 'isolated' requires that the material in question has been removed from its natural environment.

In a preferred embodiment, the amidase activity is from a peptide having at least 70% identity to the amino acid sequence as set forth in either SEQ ID No. 1 (FAAI/Dd1) or SEQ ID No. 2 (FAAII/Dd2). In other embodiments, the peptide may have at least 75% identity, at least 80% identity, at least 85% identity, at least 90% identity or at least 95% identity to the amino acid sequence as set forth in either SEQ ID No. 1 or No. 2 or is a peptide having an amino acid sequence as set forth in either SEQ ID No. 1 or SEQ ID No. 2.

It is noted that the amidase activity is isolated, meaning that it has been isolated or purified from the host organism, as discussed above. Specifically, it is noted that the host organism may be an organism that has native amidase activity such as *Dictyostelium discoideum* or may be an organism comprising an expression system arranged to express either Dd1 (SEQ ID No. 1) or Dd2 (SEQ ID No. 2) as discussed below.

Figure 3A:
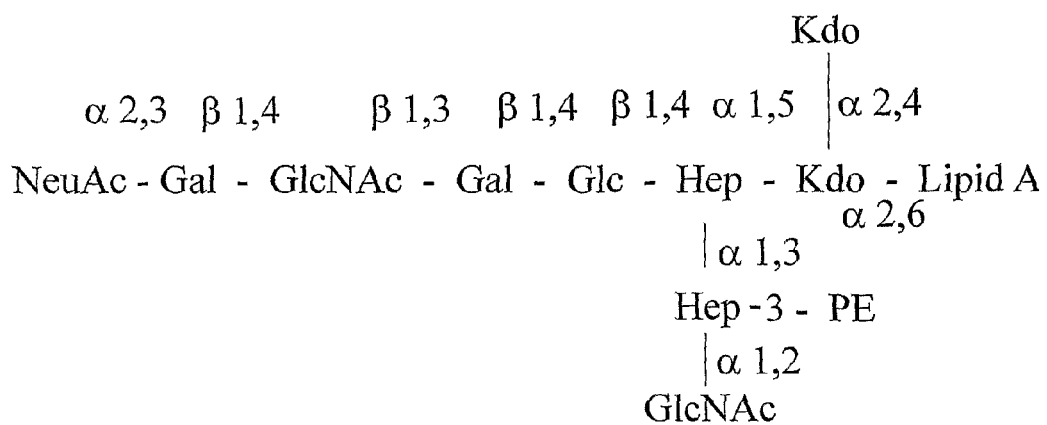
FIG. 3(a) is a schematic representation of the core oligosaccharide of the *Neisseria meningitidis* LPS molecule.
Figure 3B:
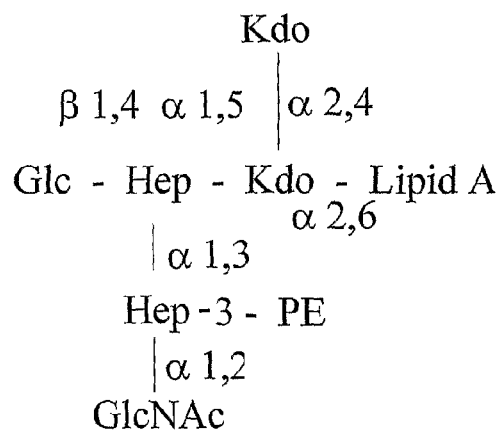
FIG. 3(b) is a schematic representation of the core oligosaccharide of the *Neisseria meningitidis* mutant strain galE LPS molecule.
Figure 3C:
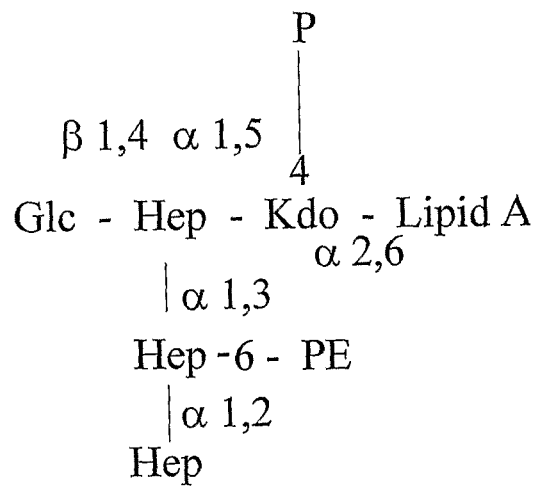
FIG. 3(c) is a schematic representation of the core oligosaccharide of the *Haemophilus influenzae* mutant strain lic1 IpsA LPS molecule.
Figure 3D:
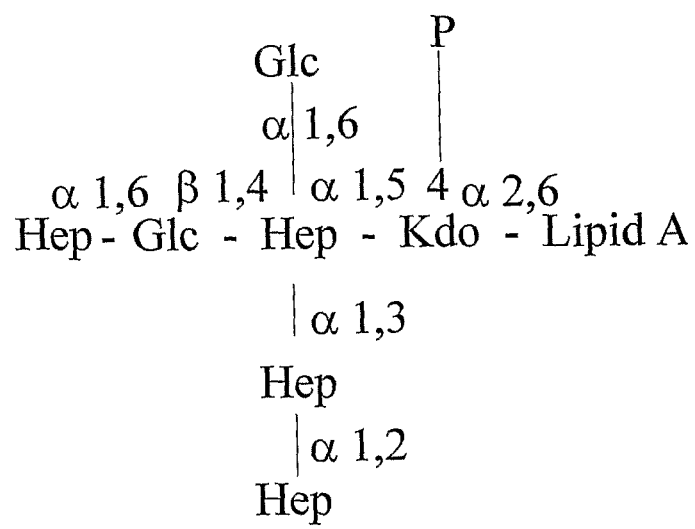
FIG. 3(d) is a schematic representation of the core oligosaccharide of the *Mannheimia haemolytica* mutant strain losB LPS molecule.

In accordance with another aspect of the invention, there is provided an isolated or purified mono-N-acylated-de-O-acylated LPS molecule or de-N-acylated-de-O-acylated LPS molecule from a bacterium of interest conjugated to a carrier protein. The a mono-N-acylated-de-O-acylated LPS molecule or de-N-acylated-de-O-acylated LPS molecule may be from any suitable Gram negative bacterium, for example, but by no means limited to *Neisseria meningitidis*, *Haemophilus influenzae* or *Mannheimia haemolytica*, as shown in FIGS. 3b, 3c and 3d. In other embodiments, the conjugate may be used for the immunization of individuals in need of such treatment, that is, individuals having or suspected of having or at risk of developing an infection from the bacterium of interest.

As discussed below, the inventors surprisingly discovered that the isolated form of the amidase is able to modify or react with substrates (LPS from specific bacterial strains) which are not substrates for the intact organism (*Neisseria meningitidis* and *Mannheimia haemolytica*). As shown in FIGS. 3b, 3c and 3d, the amidase activity works on a variety of O-deacylated substrates, including LPS from *Neisseria meningitidis*, *Haemophilus influenzae* and *Mannheimia haemolytica*.

Accordingly, in some embodiments, there is provided a purified, water-soluble O-deacylated LPS having at least one N-linked fatty acid removed. The LPS may be from *Neisseria meningitidis*, *Haemophilus influenzae* or *Mannheimia haemolytica*, which are shown in FIGS. 3b, 3c and 3d. In other embodiments, there is provided an isolated LPS as described above conjugated to a suitable carrier.

In some embodiments, the LPS is separated from, isolated from or recovered from the bacterium of interest using means known in the art, for example, by a phenol extraction and treatment with DNase, RNase and proteinases. Other suitable means known in the art may also be used.

The LPS may be de-esterfied using any suitable means known in the art, for example, enzymatically or by treatment with a suitable base, for example but by no means limited to hydrazine, mild NaOH, KOH or the like.

The modified LPS may be recovered by any suitable means known in the art, for example, by passing the material through a 10 kDa spin column and then separating further on a Sephadex G-10 chromatography column. It is noted that such methods for recovering a fraction of a specific size are well known to those of skill in the art.

Methods of conjugation and suitable carrier proteins are discussed in greater detail below.

In another embodiment of the invention, there is provided a method of recovering a modified lipopolysaccharide from a bacterium of interest comprising:

separating the lipopolysaccharide from the bacterium of interest;

de-esterfying the lipopolysaccharide layer;

removing at least one N-linked fatty acid from the lipopolysaccharide with an isolated amidase activity; and recovering the modified LPS.

In these embodiments, a modified LPS is recovered which is water-soluble as at least one of the two N-linked fatty acids has been removed and the LPS has been O-deacylated. Most importantly however, the important core components of the LPS are intact and substantially retain their native conformation or structure, as described below. Furthermore, the modified LPS is more amenable to subsequent conjugation steps, as discussed herein.

*Dictyostelium discoideum* is, a soil-living amoeba which, produces both esterases and amidases, having the specific degradative effect on LPS that is required [Verret, C R; Rev. Infect. Dis (1984) δ: 452-454]. In the natural environment *Dictyostelium discoideum* feeds on bacterial LPS, engulfing the organism, removing the fatty acids on the lipid A as its food source without any modifications to the carbohydrate groups.

Other researchers [Gustafson et al US application publication #2003/0138448 A1] have proposed using the intact *Dictyostelium discoideum* species to degrade intact bacterial species with the deacylated LPS molecule being purified from this mixture. However certain bacterial species cannot efficiently support the growth of *Dictyostelium discoideum*, including *Neisseria meningitidis*. The growth of *Dictyostelium discoideum* was examined utilising various bacterial strains as food sources. *Dictyostelium discoideum* cells were plated on a lawn of each of the following bacterial strains, capsulated *Neisseria meningitidis* L3, non-encapsulated *Neisseria meningitidis* L3, capsulated *Neisseria meningitidis* L3 galE, *Haemophilus influenzae* 1003 lic1 lpsA, *Haemophilus influenzae* 1003 lic1 lpt6, *Haemophilus influenzae* 162, *Mannheimia haemolytica* losB and *Klebsiella aerogenes* on SM and chocolate media. The growth of *Dictyostelium discoideum* on *Klebsiella aerogenes* and *Haemophilus influenzae* was normal. However, growth on *Neisseria meningitidis* whether encapsulated or not and *Mannheimia haemolytica* was severely inhibited and therefore the desired deacylated LPS molecule of *Neisseria meningitidis* and *Mannheimia haemolytica* would not be effectively produced utilising the current methodologies.

As illustrated herein it was therefore unexpected that even though *Dictyostelium discoideum* could not grow directly on *Neisseria meningitidis* and *Mannheimia haemolytica*, enzymes produced by *Dictyostelium discoideum* were capable of degrading the purified derivatives of *Neisseria meningitidis* and *Mannheimia haemolytica* LPS that we provided as substrates with the required specificity.

Figure 4:
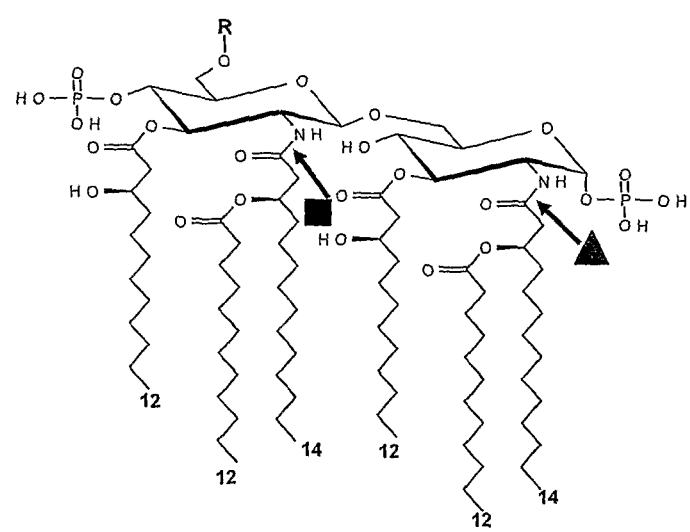
FIG. 4 is a schematic representation of location of fatty acid amidase activities on *Neisseria meningitidis* lipid A.

The enzymes disclosed herein have specific activity on residues in the lipid A region of the LPS molecule as illustrated in FIG. 4.

*Dictyostelium discoideum* acts on the Lipid A region of the LPS in a sequential manner initially utilising esterases to remove the ester linked fatty acids and then FAAI uses this O-deacylated substrate to remove the N-linked fatty acid from the GlcN-I residue and then in turn, FAAII utilises the FAAI product as its substrate to remove the N-linked fatty acid from the GlcN-II residue. All these degradative enzymatic processes are specific and do not cause any modifications to the remainder of the LPS molecule. We prepare LPS-OH, now only containing the amide linked fatty acids, and add this to the supernatant following incubation of *Dictyostelium discoideum* cells with killed *Klebsiella aerogenes* cells. *Klebsiella aerogenes* is the bacteria most commonly used as the substrate for growth of *Dictyostelium discoideum* used in the art. Incubation of the supernatant with the LPS-OH for 16 h at 22° C. and subsequent purification, as detailed in the examples, provides de-N-acylated molecules which are readily amenable to the subsequent manipulations of our conjugation strategies and most importantly contain the conserved core oligosaccharide region with no alterations to its structure. Without the enzymatic removal of the N-linked fatty acid(s) an amphiphillic molecule remains which is difficult to manipulate and produce glycoconjugates from.

Figure 6:
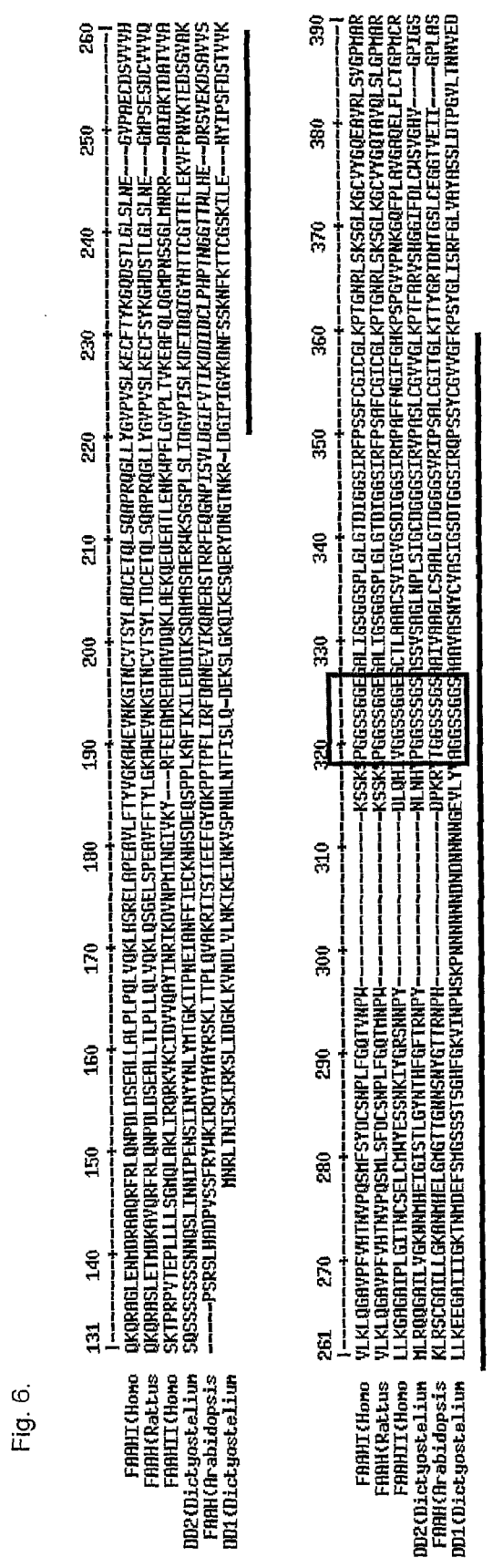

In an embodiment of the invention there are provided amino acid sequences for the two fatty acid amidases produced by *Dictyostelium discoideum* (FIG. 5): Dd1 (SEQ ID No. 1) and Dd2 (SEQ ID No. 2). These amino acid sequences were identified as amidases due to the presence of a conserved consensus amino acid sequence in both proteins, shown in FIG. 6. As shown in FIG. 6, these peptides show considerable homology to human, rat and *Arabidopsis amidases*, particularly in the amidase signature region and more specifically within the conserved GGSS(G/A/S)G motif within the amidase signature region. It will be understood that an amino acid sequence may include variants such as chemically modified amino acids, non-natural amino acids, etc.

In an embodiment of the invention there are provided nucleic acid sequences deduced from the amino acid sequences as set forth in SEQ ID No. 1 or SEQ ID No. 2, the two fatty acid amidases produced by *Dictyostelium discoideum*. The genomic sequences are shown in FIG. 7 (SEQ ID No. 3) and FIG. 8 (SEQ ID No. 4). As will be appreciated by one of skill in the art, these nucleotide sequences may be used as probes for library screening or the like, for the generation of primers, or for expression of recombinant fatty acid amidases, as discussed below. It will be readily apparent to one skilled in the art that any suitable expression system may be used.

In an embodiment of the invention there is provided a method to utilise the isolated amidase activity on the isolated O-deacylated LPS to produce molecules (FIGS. 9-16) which are carbohydrates that retain the antigenic nature of the native substrate and are useful in inducing, in a mammal, an immune response against a Gram-negative bacterium. The molecules of FIGS. 9-16 are the products of both chemical and enzymatic treatments. All the ester linked moieties have been removed from the isolated LPS molecule in the chemical step and subsequently the enzymatic step has been used to remove one or both of the amide linked fatty acids. The molecule so produced retains the phosphorylated glucosamine disaccharide of the lipid A but has lost the ester linked fatty acids and one or both of the amide linked fatty acids, this renders the molecule completely non-toxic. The core oligosaccharide has lost any ester linked moieties but has not been modified in any other way. This molecule retains antigenic epitopes that are identically conformed as they are on the surface of the bacterial cell, as monoclonal antibodies to the native LPS structures and whole bacterial cells also recognise the molecules depicted in FIGS. 9-16.

In an embodiment of the invention there is provided an LPS-derived product obtainable by activity of at least one of the amino acid sequence described above, and uses thereof as antigens and in the manufacture of vaccines.

In an embodiment of the invention there is provided a modified lipopolysaccharide ("LPS") molecule wherein at least one N-linked fatty acid has been removed without modification of antigenic residues in the inner core. The chemically O-deacylated and enzymatically N-deacylated molecules exemplary examples of which are shown in FIGS. 9-16 are then utilised in conjugation strategies whereby they are ultimately linked to a carrier protein.

In an embodiment of the invention there is provided a modified LPS molecule above wherein at least the glycosidic phosphate group from the lipid A has also been removed.

In an embodiment of the invention there is provided a modified LPS molecule substantially free of fatty acids linked to the Lipid A region and having a linker attached to an aldehydro group. The aldehydro group will preferably have been made available by removal of a phosphate group. The generation of the aldehydro group creates a specific functionality available for conjugation away from the antigenic epitopes of the core oligosaccharide.

In some scenarios the carbohydrate molecule may be linked to a carrier protein via a linker molecule. The linker molecule may be but is not restricted to squarate, cystamine, N-succinimidyl 3-maleimidopropionate, adipic acid dihydrazide, ε-aminohexanoic acid, chlorohexanol dimethyl acetal, D-glucuronolactone and p-nitrophenylamine. As will be apparent to one of skill in the art, other suitable linker molecules may be used.

In one embodiment cystamine is chosen as the linker as it terminates with a thiol moiety which would facilitate conjugation via sulphur chemistry and therefore not involve any of the amino groups in the carbohydrate molecule, modification of which would alter antigenic epitopes in the derived glycoconjugate.

This carrier protein may be but is not restricted to $CRM_{197}$, tetanus toxoid (TT), diphtheria toxoid, HSA, BSA, detoxified P. aeruginosa toxin A, cholera toxin/toxoid, pertussis toxin/toxoid, Clostridium perfringens exotoxins/toxoid, hepatitis B surface antigen, hepatitis B core antigen, rotavirus VP 7 protein, N19 polyepitope, respiratory syncytial virus F and G proteins. As will be apparent to one skilled in the art, other suitable carrier proteins may be used.

In some cases the carrier protein may be activated. Activating agents include but are not restricted to 3,3'-Dithiodipropionic acid di-N-hydroxysuccinimide ester (DTSP) and N-succinimidyl-bromo-acetate. As will be apparent to one skilled in the art, other suitable activating agents may be used.

In an embodiment of the invention there is provided a method of inducing an immune response in a mammal comprising administering an antigen comprising a modified LPS molecule substantially free of fatty acids linked to the Lipid A region.

The glycoconjugate is then administered to a mammal in the presence of an adjuvant. The adjuvants to be utilised include but are not restricted to alum, MF59 (squalene) and archaeosomes. As will be apparent to one skilled in the art, other suitable adjuvants may be used.

Bacterial species and the diseases they cause that could be targeted by such a strategy could include, but are not restricted to Neisseria meningitidis (meningitis), Haemophilus influenzae (otitis media), Mannheimia haemolytica (ovine and bovine pneumonic pasteurellosis (shipping fever) and ovine septicemia), Actinobacillus pleuropneumoniae (porcine fibrinohemorrhagic necrotizing pleuropneumoniae) and Pasteurella multocida (avian fowl cholera, bovine hemorrhagic septicemia, porcine atrophic rhinitis). Antibodies generated to the immunising glycoconjugate would be T-cell dependent and have immunological memory, so that when the antibody specific bacterial antigen is exposed to the immune system a rapid antibody response would facilitate recognition and killing of the foreign antigen.

The invention will now be illustrated by way of examples. However, it is to be understood that the examples are for illustrative purposes and are not necessarily limiting.

Example 1

Ability of Dictyostelium discoideum to Grow on Several Gram-Negative Bacteria

Several Gram-negative bacteria were grown on chocolate agar and SM media plates and Dictyostelium discoideum was seeded in the corner of each plate and incubated at 22° C. in order to observe if the bacterial culture could support growth of Dictyostelium. As Table 1 shows Neisseria meningitidis, whether capsulated or non-capsulated and Mannheimia haemolytica were unable to support growth whereas Klebsiella aerogenes and Haemophilus influenzae were able to support growth.

TABLE 1

Growth of Dictyostelium on Gram-negative bacterial cells

| Bacteria | Media | Growth[1] |
|---|---|---|
| Neisseria meningitidis L3 galE | SM | * |
| | Chocolate | − |
| Neisseria meningitidis L3 capsulated | SM | * |
| | Chocolate | − |
| Neisseria meningitidis L3 non-capsulated | SM | * |
| | Chocolate | − |
| Haemophilus influenzae 1003 lic1 lpsA | SM | * |
| | Chocolate | +++ |
| Haemophilus influenzae 1003 lic1 lpt6 | SM | * |
| | Chocolate | ++ |
| Haemophilus influenzae 162 | SM | * |
| | Chocolate | ++ |
| Mannheimia haemolytica losB | SM | +/− |
| | Chocolate | +/− |
| Klebsiella aerogenes | SM | +++ |
| | Chocolate | +++ |

[1]+++, excellent growth; ++, growth; +, poor growth; −, no growth; * no bacterial growth on this media.

Example 2

Fatty Acid Amidases (FAAI and FAAII) and the Genes Encoding FAAI and FAAII Deduced from the Dictyostelium discoideum Genome Sequence Two fatty acid amidases were identified from the Dictyostelium discoideum genome (FIGS. 5a (SEQ ID No. 1) and 5b (SEQ ID No. 2)) by virtue of their consensus amidase sequences FIG. 6). BLASTp analysis revealed that Dd1 and Dd2 were homologous to mammalian amidase (human), (Dd1: 27% identical, 42% similar; Dd2: 32% identical, 43% similar). Additionally Dd1 and Dd2 were found to be 22% identical and 41% similar to each other. Alignment comparison between Dd1, Dd2 and human amidase was determined using a multalign software program (F. Corpet, 1988, Nucl. Acids Res., 16 (22), 10881-10890), and is shown in FIG. 6.

The genomic DNA sequences for the two genes are as shown in FIGS. 7 (SEQ ID No. 3) and 8 (SEQ ID No. 4).

Example 3

Cloning and Expression of Dd1 Gene in *Escherichia coli*

Gene Dd1 was obtained by PCR using genomic DNA of *Dictyostelium* as template. Gene specific primers used were NRC 191
(SEQ ID No. 5)
(5'CTCGAGAATAGATTAACAAATATATCAAAAATTAGAAAATC 3')
and NRC 192
(SEQ ID No. 6)
(5'GTCGACTTATTTTAAATAATTTGGTGTAAGTGATGTAAAATC 3').

NRC 191 and NRC 192 introduce restriction sites XhoI at the 5' end and SalI at the 3' end respectively of the Dd I gene. The restriction sites were designed for cloning the Dd I gene into the protein expression vector pNRC71. The PCR conditions used to amplify the Dd1 gene were as follows: —

| Denaturation - | 92° C. for 30 s |
| Annealing - | 52° C. for 1 min |
| Extension - | 68° C. for 2 min |

Figure 17:
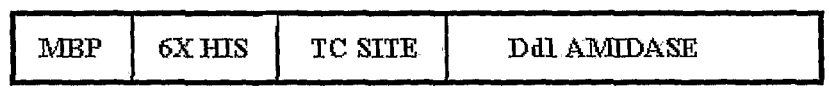
FIG. 17 is a schematic representation of the cloned Dd1 gene
Figure 18:
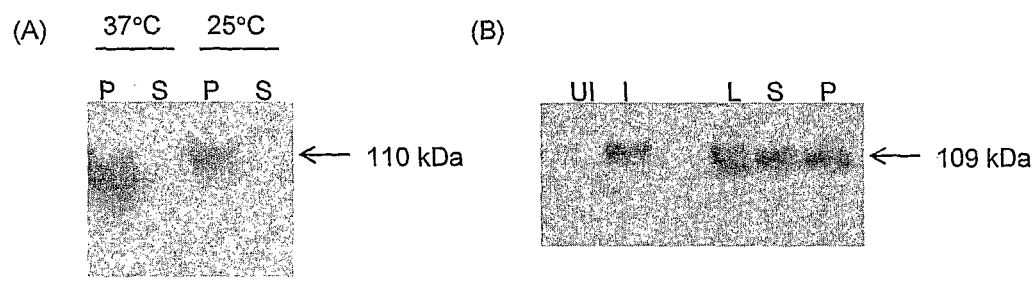
FIG. 18 is a SDS-PAGE analysis of recombinant Dd1-MBP-6× His fusion protein expressed in *E. coli*

For 25 cycles with a final extension step for 10 min at 68° C. The PCR product obtained with the above set of primers was cloned into the pCR2.1 plasmid (TA cloning kit, Invitrogen) and transformed into *E. coli* strain TOP10F' (Invitrogen). The right clones obtained with Dd1 gene insert were restricted with XhoI/SalI and cloned into the protein expression vector pNRC71 (which encode maltose binding protein (MBP)-6× His-thrombin cleavage site at the N-terminus of the fusion protein) and transformed into *E. coli* strain BL21 cells (Novagen). The recombinant Dd 1 protein expressed as MBP-6× His fusion protein (FIG. 17) was purified by amylose resin affinity chromatography using BioLogic chromatography system from BioRad. The purified fusion protein which contains MBP and a 6× His tag at the N-terminus was proteolytically digested with thrombin. The thrombin cleaved MBP protein containing the 6× His tag was removed by passing on to a Ni-NTA column by affinity chromatography. The flow through contained pure Dd1 protein. The over expressed recombinant protein was confirmed by Western blot analysis using anti polyhistidine antibody (Sigma) (FIG. 18a).

Cloning and Expression of Dd1($\Delta$1-11) MBP Fusion Protein.

As the full length recombinant Dd1-MBP fusion protein was expressed as an insoluble protein in *E. coli* inclusion bodies, which required additional solubilization procedures to extract the protein, another alternative approach producing a truncated Dd1-MBP fusion protein lacking the first 11 amino acid was adopted. Truncated Dd1 protein which lacked the first 11 amino acids at the N-terminus was cloned as MBP-6× His fusion protein. Gene specific primers NRC197 (5'CTCGAGAAATCATTTTAGATGGAAAA3') (SEQ ID No. 7) and NRC 198 (5'GTCGACTTATTTTAAATTTTTG-GTGT3') (SEQ ID No. 8) were used to PCR amplify the gene using genomic DNA of *Dictyostelium* as template. The PCR conditions used was same as the above used to amplify full length Dd1 gene. NRC 197 and NRC 198 introduce restriction sites XhoI at the 5' end and SalI at the 3' end respectively of the Dd I gene. The restriction sites were designed for cloning the Dd I gene into the protein expression vector pNRC71.

The obtained recombinant protein was purified by amylose resin affinity chromatography using BioLogic chromatography system from BioRad. The purified fusion protein which contains MBP and a 6× His tag at the N-terminus was proteolytically digested with thrombin. The thrombin cleaved MBP protein containing the 6× His tag was removed by passing on to a Ni-NTA column by affinity chromatography. The flow through collected contained pure $\Delta$1-11 Dd1 protein. The over expressed recombinant protein was confirmed by Western blot analysis using anti polyhistidine antibody (Sigma) (FIG. 18b).

Example 4

Cloning and Expression of Dd2 Gene in *Escherichia coli*

Dd 2 Gene was Obtained by Reverse Transcription Polymerase Chain Reaction (RT-PCR)

Figure 19:
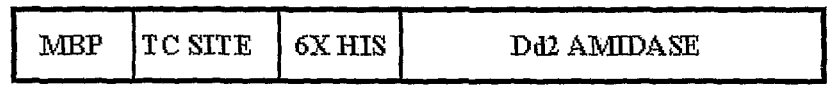
FIG. 19 is a schematic representation of the cloned Dd2 gene
Figure 20:
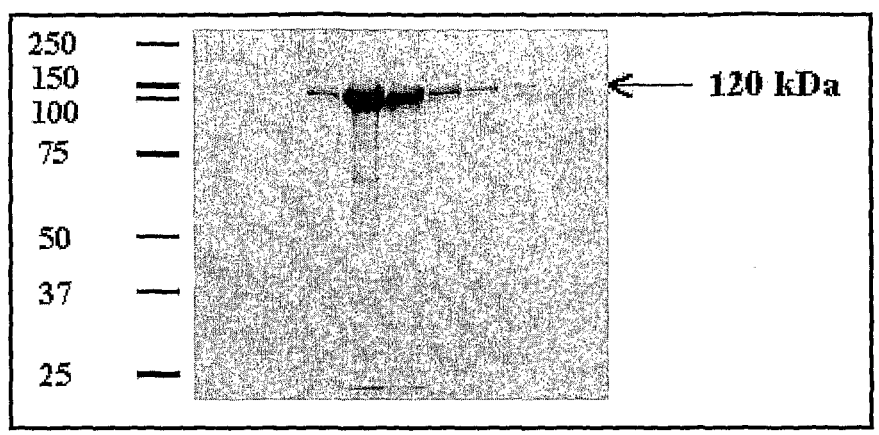
FIG. 20 is a SDS-PAGE analysis of recombinant Dd2-MBP-6× His fusion protein expressed in *E. coli*

*Dictyostelium* cells grown utilizing *Klebsiella aerogenes* as food source were harvested and used to isolate RNA. Total RNA from *Dictyostelium* cells was isolated using RNeasy Midi kit (Qiagen). The RNA isolated was quantitated and 2 µg of RNA was used in the Reverse-Transcription reaction. The Gene specific primer NRC 190 (5' GTCGACTTAGT-TATTTGGGTTTGTGCTTTTG) (SEQ ID No. 9) was used in the Reverse Transcription reaction to obtain the cDNA. The cDNA obtained was used as the template in the subsequent PCR to amplify Dd2 gene using gene specific primers NRC189 (5'CATATGCACCACCATCATCACCACA-CATCTTCTTCATTTGTAAAAGTAGTA G 3') (SEQ ID No. 10) and NRC190. NRC 189 introduces restriction site NdeI as well as 6×HIS tag at the 5' end and NRC 190 introduces SalI at the 3' end of the Dd2 gene. The PCR product obtained using the above set of primers was cloned into the pCR2.1 plasmid (TA cloning kit, Invitrogen) and transformed into *E. coli* TOP10F' (Invitrogen). The right clones obtained with the His$_6$-Dd2 insert were restriction digested with NdeI/SalI and cloned into pCW-MaIET vector, which encodes MBP-Thrombin cleavage site at the N-terminus of Dd2 protein. The recombinant Dd 2 protein expressed as MBP-6× His fusion protein (FIG. 19) was purified by amylose resin affinity chromatography using BioLogic chromatography system from BioRad. The purified fusion protein which contains MBP at the N-terminus of Dd2 protein was removed by cleaving the purified fusion protein with thrombin. The recombinant Dd2 protein containing a 6× His tag at the N-terminus was separated from cleaved MBP by passing on to a Ni-NTA column by affinity chromatography and the elution profile examined by a Coomassie-stained gel (FIG. 20).

Example 5

Amidase Activity of Recombinant Dd1 & 2

Figure 21:
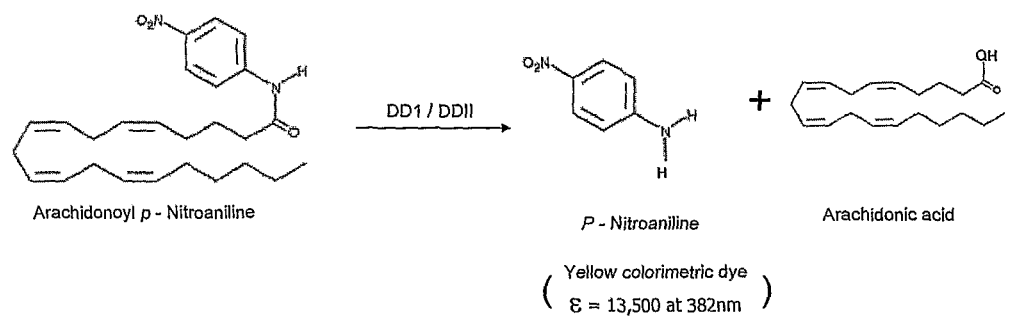
FIG. 21 is a schematic representation of the calorimetric assay for recombinant Dd1 and Dd2 amidase activity

The enzymatic activity of the fatty acid amidase homologues Dd 1 and Dd 2 were established by using synthetic substrate arachidonoyl p-nitroaniline (Cayman chemical, USA) (FIG. 21).

The enzyme activity using synthetic substrate was determined by monitoring the release of p-nitroaniline at 382 nm (E=13500 m$^{-1}$ cm$^{-1}$) on a UV—visible spectrophotometer.

The amidase activity of Dd1 and Dd2 was confirmed by initiating the reaction by adding 100 ul of recombinant proteins Dd1 or 2 (1 mg/ml in 20 mM Tris pH 7.4) to 160 ul of reaction buffer (125 mM Tris pH8.0 and 1 mMEDTA) followed by the addition of 20 ul of substrate (10 mg/ml in 75% DMSO). Recombinantly expressed Dd1 and Dd2 both caused release of p-nitroaniline as revealed by formation of a yellow colour on reaction with the synthetic substrate.

Example 6

Production of Antisera to Recombinant Dd2 Protein and Analysis of In Vivo Expression of Dd2 in *Dictyostelium* Cells Polyclonal antiserum (NRC-Dd2) was raised against recombinant Dd2 protein expressed in *E. coli*. The recombinant protein expressed as MBP-6× His fusion protein was purified by amylose resin affinity chromatography. MBP present at the N terminus of the purified protein was removed by cleavage with thrombin. The protein free from MBP was separated by passing on to a Ni-NTA column and the pure protein obtained was used to immunize New Zealand white rabbits (100 g per immunisation at day 0, 14 and 28). The polyclonal antisera obtained recognized a 70 kDa protein in *Dictyostelium* cell lysates, which is the expected size of the translated protein (FIG. 22).

More specifically the antisera was also able to pull down the 70 kDa in vivo protein from amidase active purified supernatant from *Dictyostelium* cell lysates by immunoprecipitation. The immunoprecipitated protein sequence was confirmed as the 70 kDa amidase by MALDI-TOF MS amino acid sequence analysis following excision and tryptic digestion of the specific band from a Coomassie stained gel (FIG. 23), confirming that the recombinant Dd2 is the amidase protein.

Example 7

Over Expression of Dd1 and Dd2 in *Dictyostelium*

Because Dd1 and Dd2 are eukaryotic enzymes, which when over expressed in *E. coli* may not be optimally functional due to the necessity of post-translational modification or any other activating factors present in the host for complete activity, *Dictyostelium discoideum* over-expression vectors to express Dd1 and Dd2 in *Dictyostelium discoideum* itself are preferably utilised. Gene Dd1 was obtained by PCR using genomic DNA of *Dictyostelium* as template. Gene specific primers used were NRC 193
(SEQ ID No. 11)
(5'GAATTCATGAATAGATTAACAAATATATCAAAAATTAGAAAAT C 3')
and NRC 194
(SEQ ID No. 12)
(5'AAGCTTTTAGTGATGATGGTGATGATGTTTTAAATAATTTGGTGTAA

GTGAT 3'.

NRC 193 and 194 introduce restriction sites EcoRI at the 5' end and HindIII at the 3' end respectively of the Dd I gene. The restriction sites were designed for cloning the Dd1 gene into the *Dictyostelium* protein expression vector pDEXRH. Gene Dd2 was PCR amplified using Dd2 cDNA obtained by reverse transcription reaction of mRNA from *Dictyostelium* cells using gene specific primer NRC 190 (5' GTCGACT-TAGTTATTTGGGTTTGTGCTTTTG3') (SEQ ID No. 9). For PCR amplification primers NRC195 (5' AAGCTTATGA-CATCTTCTTCATTTGTAAAAGTAG3') (SEQ ID No. 13) and NRC196 (5'MGCTTTTAGTGATGATGGTGATGATG-GTTATTTGGGTTTGTGCCTTTTGTT 3') (SEQ ID No. 14) were used. NRC195 and 196 introduce restriction sites HindIII both at the 5' end and 3' end of the gene, which enables to clone Dd2 gene in pDEXRH vector at HindIII site. Both Dd1 and Dd2 genes were cloned in *Dictyostelium* protein expression pDEXRH vector and transformed into *Dictyostelium*. The expression level of the recombinant protein is very low. Alternatively, Dd1 and Dd2 are also cloned with a 6× His tag at the N-terminus in pVS4 vector. An advantage of using *Dictyostelium discoideum* pVS4 vector is that it encodes a cleavable secretary signal peptide at the N-terminus of the fusion protein. By this method the over-expressed protein that is secreted in the culture medium is readily purified using Ni-NTA affinity chromatography.

Example 8

Isolation and Activity of FAAI Directly from *Dictyostelium discoideum*

*Dictyostelium discoideum* was grown to logarithmic phase ($3\times10^6$ cells/ml) in liquid AX2 media (pH 6.7; 7.15 g/l yeast extract, 14.3 g/l peptone, 18.6 g/l maltose, 0.486 g/l $KH_2PO_4$, 0.616 g/l $Na_2HPO_4.2H_2O$). The cells were harvested and washed 2× with PBS and immediately suspended in PBS with phenol-killed and PBS washed cells of *Klebsiella aerogenes* to continue their growth, now utilising *Klebsiella aerogenes* as a food source with O-deacylated LPS (LPS-OH) supplied as an additional substrate.

When *Dictyostelium discoideum* was allowed to grow in the presence of *Klebsiella aerogenes* for 24 h, it was expected to produce amidase activity. The ratio of the number of bacterial cells and *Dictyostelium discoideum* cells that optimised N-deacylation of the purified LPS-OH substrate was standardised to $1\times10^{11}$ vs. $5\times10^7$ cells/ml respectively.

Therefore to utilise these enzymes during growth of *Dictyostelium discoideum*, LPS-OH isolated from the Gram-negative bacterium *Neisseria meningitidis* immunotype L3 galE mutant was added to the *Klebsiella aerogenes/Dictyostelium discoideum* mixture.

Figure 9:
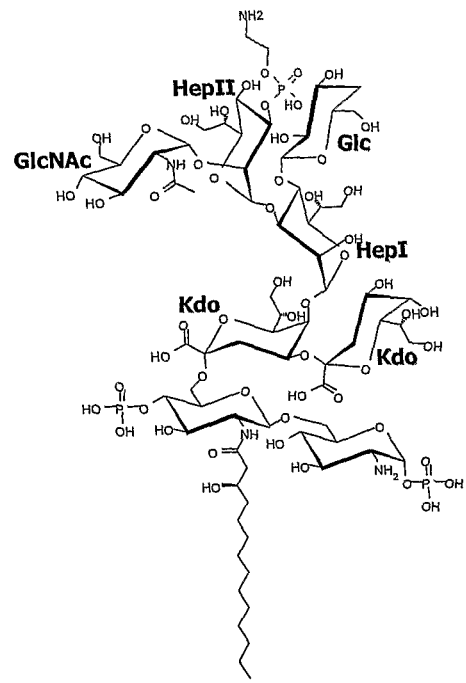
FIG. 9 is a structural representation of mono-N-acylated-de-O-acylated LPS molecule from *Neisseria meningitidis* strain L3 galE.
Figure 10:
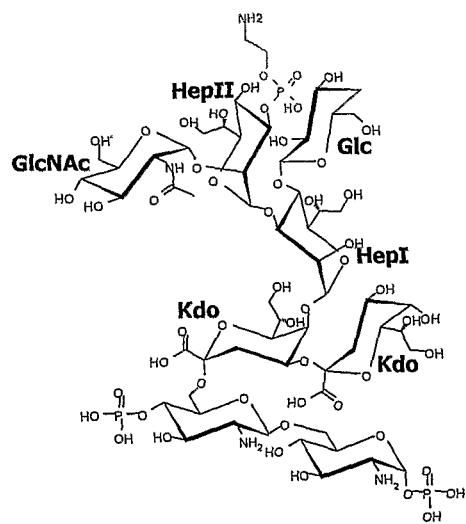
FIG. 10 is a structural representation of de-N-acylated-de-O-acylated LPS molecule from *Neisseria meningitidis* strain L3 galE.
Figure 11:
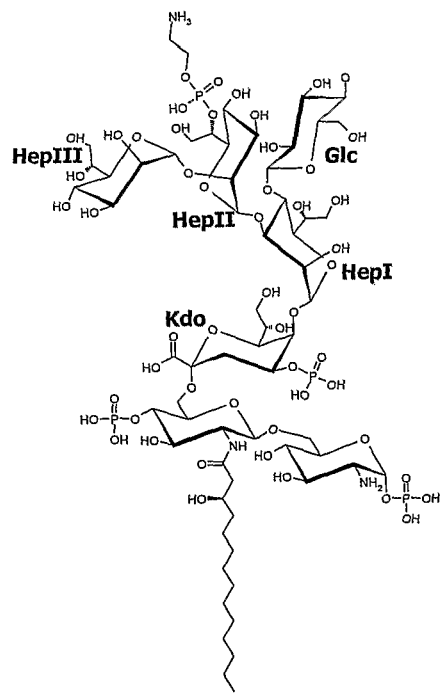
FIG. 11 is a structural representation of mono-N-acylated-de-O-acylated LPS molecule from *Haemophilus influenzae* strain 1003 lic1lpsA.
Figure 12:
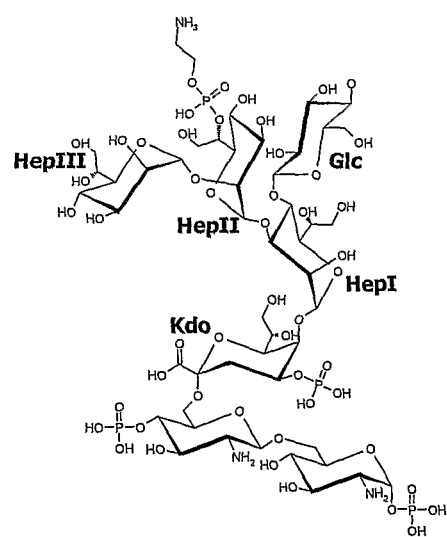
FIG. 12 is a structural representation of de-N-acylated-de-O-acylated LPS molecule from *Haemophilus influenzae* strain 1003 lic1lpsA.
Figure 13:
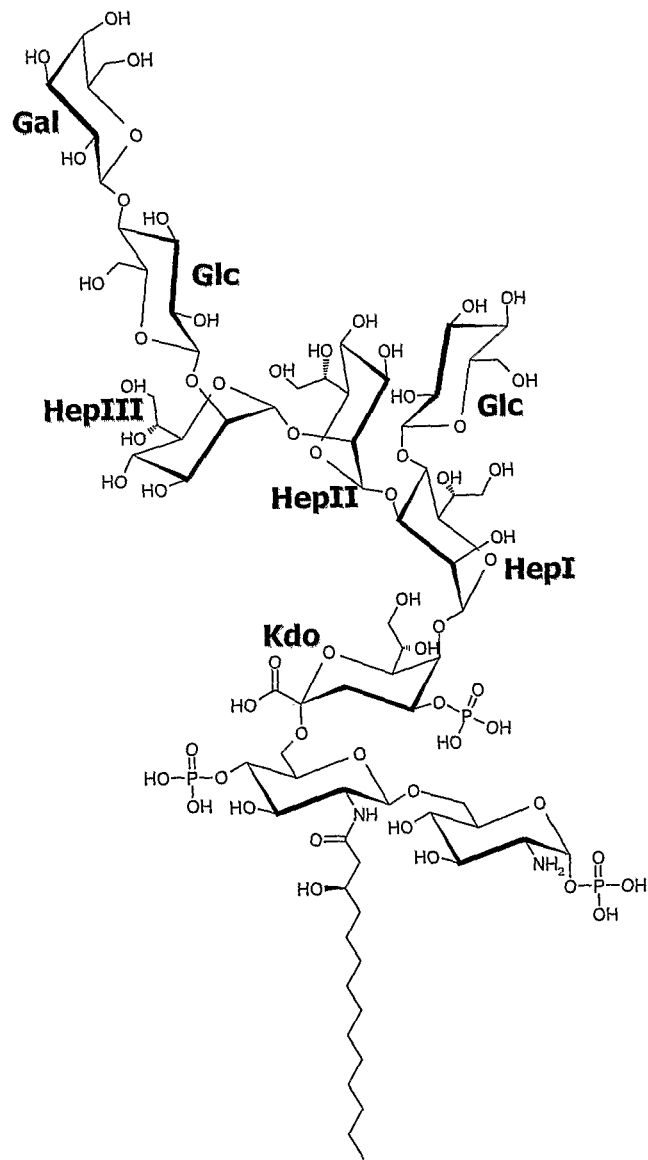
FIG. 13 is a structural representation of mono-N-acylated-de-O-acylated LPS molecule from *Haemophilus influenzae* strain 1003 lic1lpt6.
Figure 14:
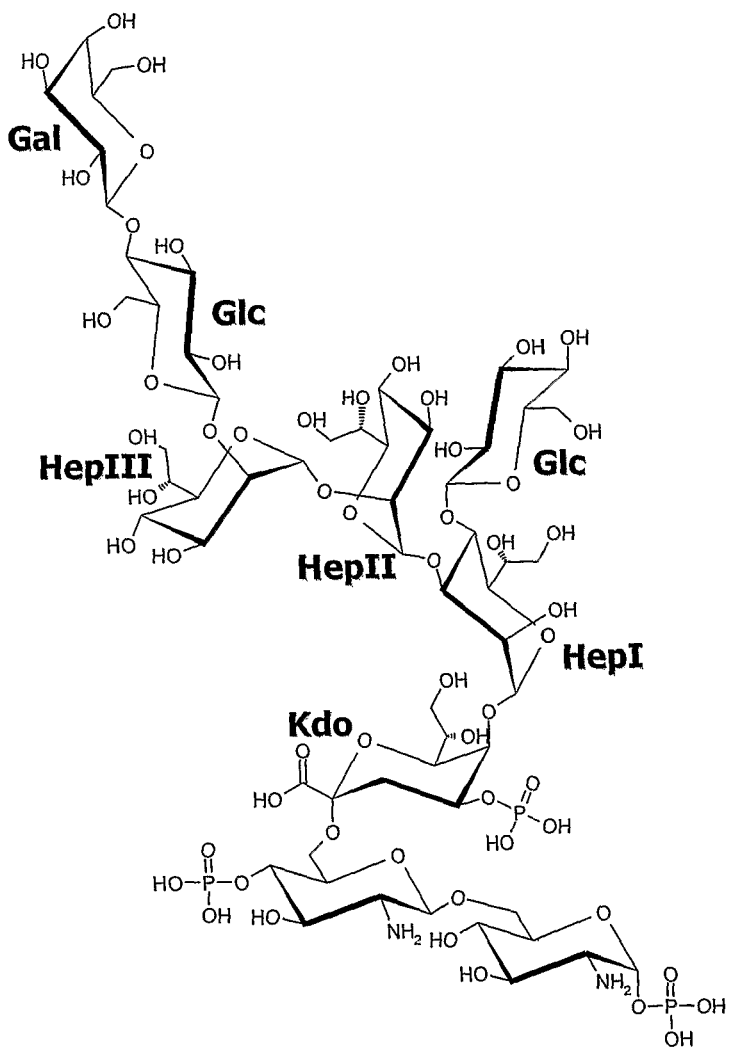
FIG. 14 is a structural representation of de-N-acylated-de-O-acylated LPS molecule from *Haemophilus influenzae* strain 1003 lic1lpt6.
Figure 15:
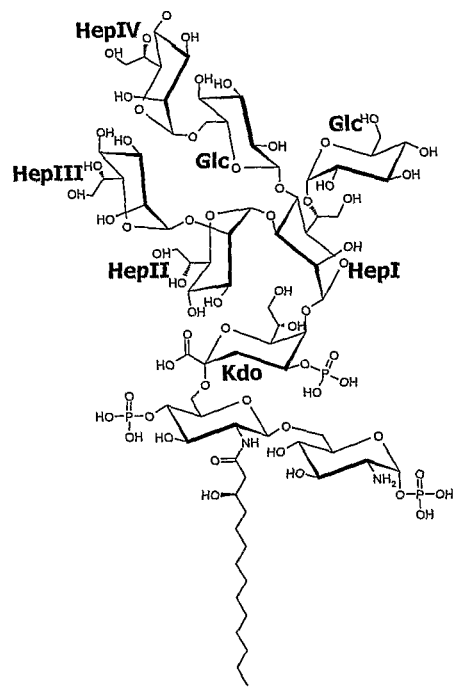
FIG. 15 is a structural representation of mono-N-acylated-de-O-acylated LPS molecule from *Mannheimia haemolytica* strain losB.
Figure 16:
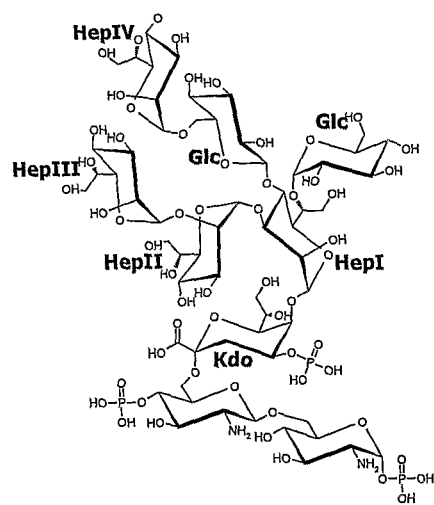
FIG. 16 is a structural representation of de-N-acylated-de-O-acylated LPS molecule from *Mannheimia haemolytica* strain losB.
Figure 24:
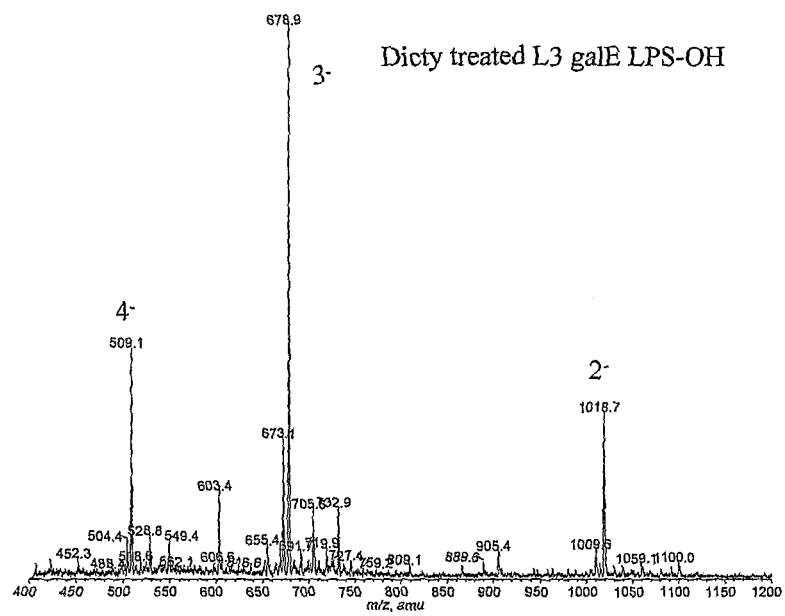
FIG. 24 is the CE-MS spectrum of *Neisseria meningitidis* strain L3 galE O-deacylated LPS, after treatment with isolated *Dictyostelium discoideum* amidases following growth of *Dictyostelium* with *Klebsiella aerogenes*.

The expected products following *Neisseria meningitidis* L3 galE LPS-OH incubation with the supernatant from growth of *Dictyostelium discoideum* and *Klebsiella aerogenes* are detailed in FIGS. 9 and 10, and this was confirmed when the starting material and reaction products were examined by capillary electrophoresis electrospray-mass spectrometry (CE-ES-MS) (FIG. 24).

In some instances it will be preferable to retain the second N-linked fatty acid, although the structure lacking this second fatty acid may still be desired in some situations. For use in preparing a vaccine, the structure containing the second fatty acid may be preferred.

Following 24 h incubation of *Neisseria meningitidis* L3 galE LPS-OH to the suspension of *Dictyostelium discoideum* and *Klebsiella aerogenes* at 22° C. with agitation, the cells were pelleted and the supernatant was lyophilised and examined by CE-ES-MS (FIG. 24).

The doubly charged ion at m/z $1018.7^{2-}$ and the triply charged ion at $678.9^{3-}$ -corresponds to a molecular weight of 2039.4 amu consistent with the composition 2GlcN, 1 FA, 2P, 2 Kdo, 2Hep, GlcNAc, PEtn as illustrated in the schematic above. The doubly charged ion at m/z 905.4$^{2-}$ corresponds to the loss of the second fatty acid residue from the lipid A region.

The product from exposure of Neisseria meningitidis L3 galE LPS-OH to the Dictyostelium discoideum / Klebsiella aerogenes suspension therefore has a molecular weight of at least 225 amu smaller than the LPS-OH substrate. This is consistent with the absence of a N-linked fatty acid (3-hydroxy myristic acid) from the lipid A region of the molecule.

This was confirmed by a tandem mass spectrometry technique, which can specifically fragment selected ions from the primary mass spectrum. The nature of LPS-OH and derived molecules is such that fragmentation is enhanced between the lipid A region and the core oligosaccharide molecule, with the size of the fragmented lipid A region being indicated in the resulting mass spectrum. In this way one can compare the size of the lipid A region from intact LPS-OH to that of the product from LPS-OH exposure to the Dictyostelium discoideum/ Klebsiella aerogenes suspension.

Figure 25:
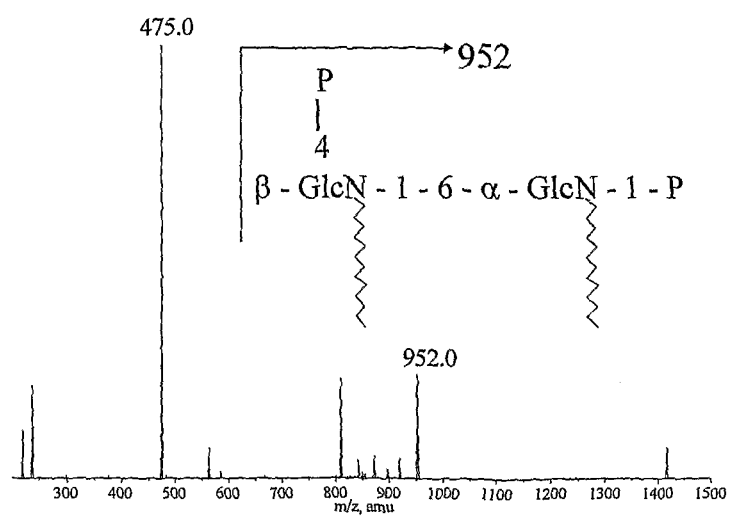
FIG. 25 is the CE-MS-MS spectrum of *Neisseria meningitidis* strain L3 galE O-deacylated LPS, revealing lipid A size consistent with the presence of two N-linked fatty acids.

As FIG. 25 illustrates, an intact LPS-OH molecule fragments to give ions for the lipid A region of m/z 952$^-$ and 475$^{2-}$. These ions of m/z 952$^-$ and 475$^{2-}$ correspond to two glucosamine sugars, two phosphate groups and two N-linked fatty acid moieties.

Figure 26:
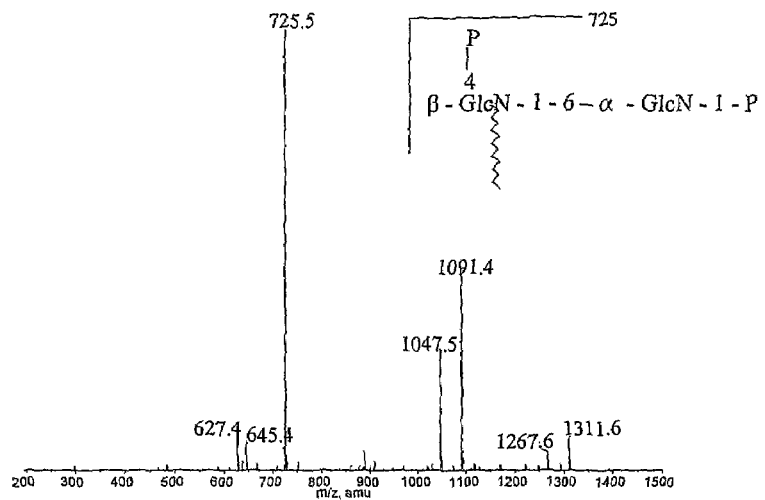
FIG. 26 is the CE-MS-MS spectrum of *Neisseria meningitidis* strain L3 galE O-deacylated LPS after treatment with *Dictyostelium discoideum* amidase, revealing lipid A size consistent with the presence of one N-linked fatty acids.

However, MS/MS analysis of the doubly charged ion at m/z 1018.7$^{2-}$ from the Dictyostelium discoideum/Klebsiella aerogenes exposed LPS-OH molecule (FIG. 26) causes fragmentation to give a singly charged ion for the lipid A region of m/z 725$^-$. This ion of m/z 725$^-$ corresponds to two glucosamine sugars, two phosphate groups and one N-linked fatty acid moiety, thus illustrating that a N-linked fatty acid has been removed from the lipid A region of the LPS-OH following exposure to the Dictyostelium discoideum/Klebsiella aerogenes suspension. The core oligosaccharide is still completely intact as indicated by the singly charged ion at m/z 1311.6 that corresponds to a composition of 2 Kdo, 2Hep, PEtn, GlcNAc, Glc and the loss of one Kdo residue (due to the labile nature of the ketosidic bond in the MS fragmentation step) to give the singly charged ion at m/z 1091.

Figure 27:
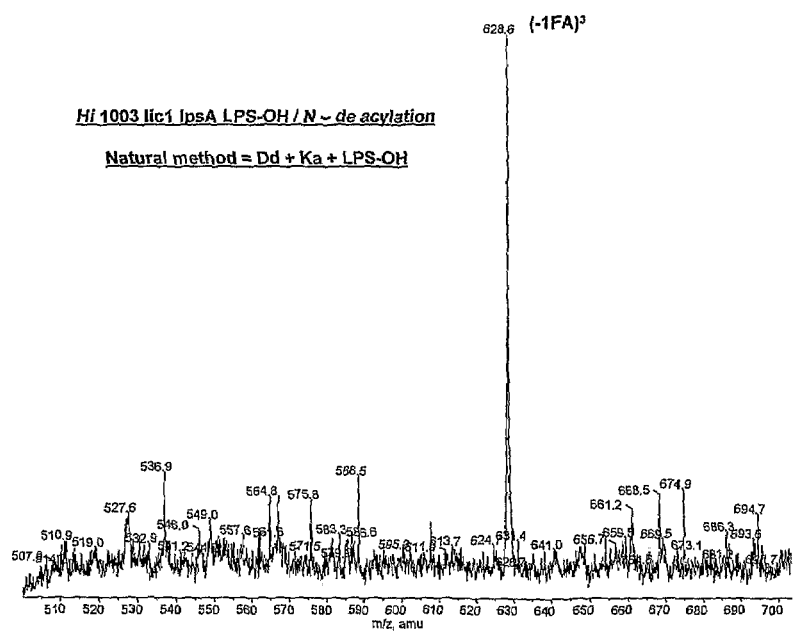
FIG. 27 is the CE-MS spectrum of *Haemophilus influenzae* strain 1003 lic1lpsA O-deacylated LPS, after treatment with isolated *Dictyostelium discoideum* amidases following growth of *Dictyostelium* with *Klebsiella aerogenes*.
Figure 28:
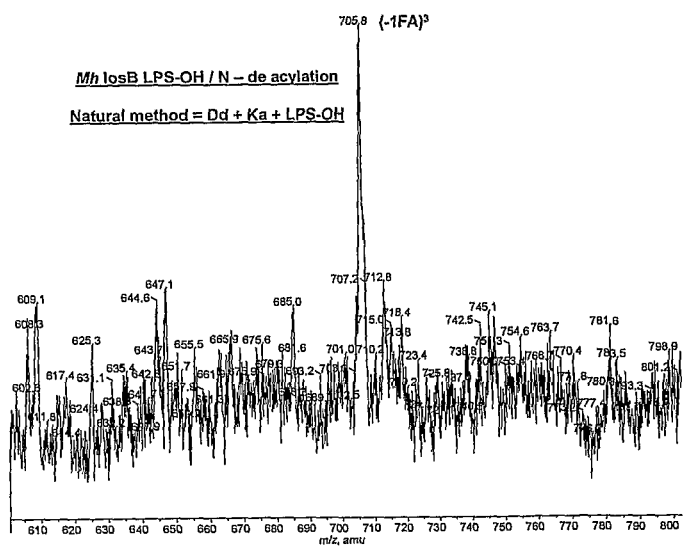
FIG. 28 is the CE-MS spectrum of *Mannheimia haemolytica* strain losB O-deacylated LPS, after treatment with isolated *Dictyostelium discoideum* amidases following growth of *Dictyostelium* with *Klebsiella aerogenes*.

This mono-acylated molecule can be exploited for the development of glycoconjugates or utilised as a substrate for the second amidase FAAII. This method to induce Dictyostelium discoideum to produce the FAAI activity has been reproducibly produced with several purified LPS-OH molecules from different species including Haemophilus influenzae (FIG. 27) and Mannheimia haemolytica (FIG. 28) so long as the ratio of Dictyostelium discoideum:Klebsiella aerogenes cell numbers was maintained at 5×10$^7$:1×10$^{11}$ cells/ml respectively.

Alternatively amidase activity was isolated directly from starved Dictyostelium cells. It is well known that Dictyostelium secretes various factors to survive conditions of starvation, and we have observed that it also secretes amidases during starvation.

Figure 29:
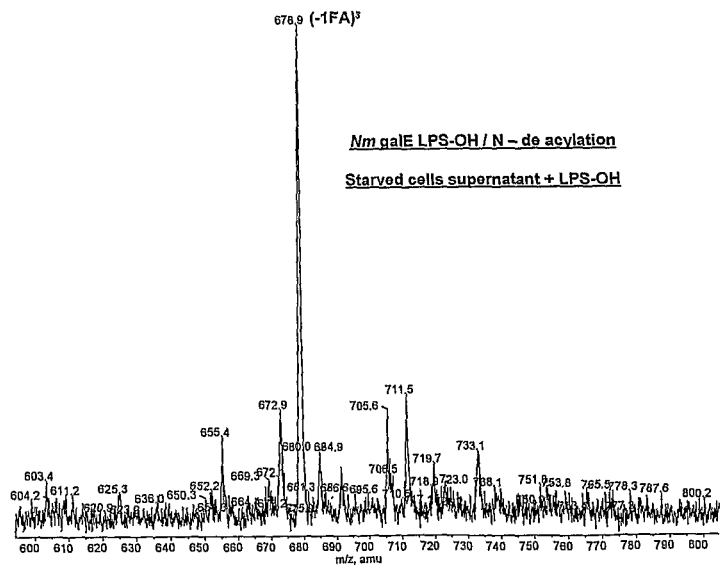
FIG. 29 is the CE-MS spectrum of *Neisseria meningitidis* strain L3 galE O-deacylated LPS, after treatment with isolated *Dictyostelium discoideum* amidases following starvation of *Dictyostelium*
Figure 30:
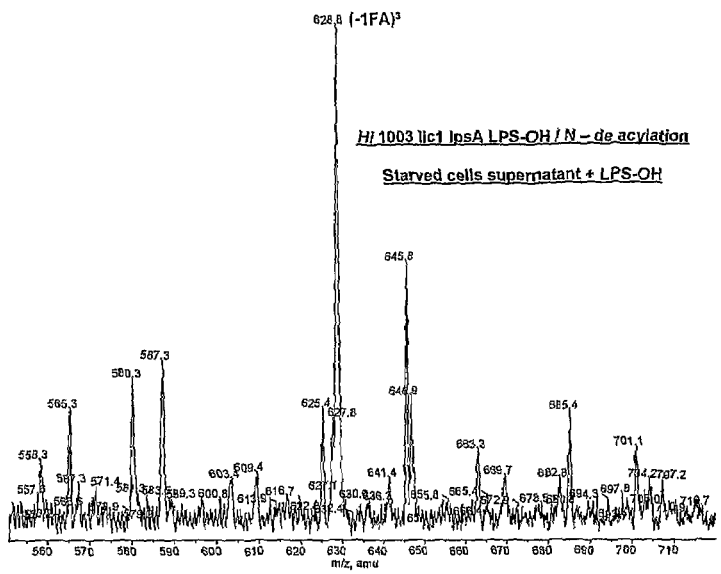
FIG. 30 is the CE-MS spectrum of *Haemophilus influenzae* strain 1003 lic1lpsA O-deacylated LPS, after treatment with isolated *Dictyostelium discoideum* amidases following starvation of *Dictyostelium*
Figure 31:
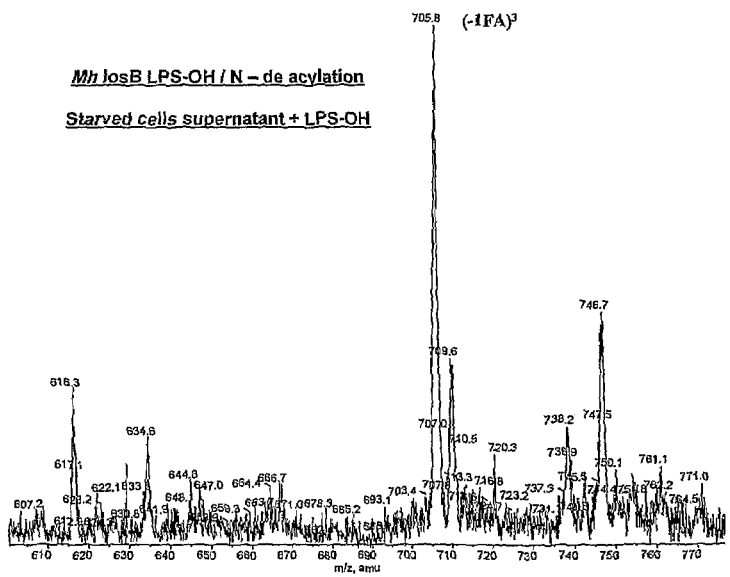
FIG. 31 is the CE-MS spectrum of *Mannheimia haemolytica* strain losB O-deacylated LPS, after treatment with isolated *Dictyostelium discoideum* amidases following starvation of *Dictyostelium*
Figure 32:
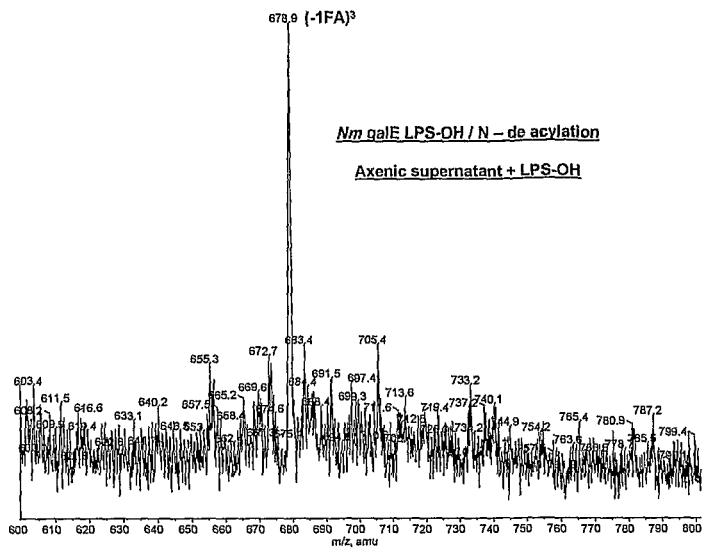
FIG. 32 is the CE-MS spectrum of *Neisseria meningitidis* strain L3 galE O-deacylated LPS, after treatment with isolated *Dictyostelium discoideum* amidases following growth of *Dictyostelium axenically*
Figure 33:
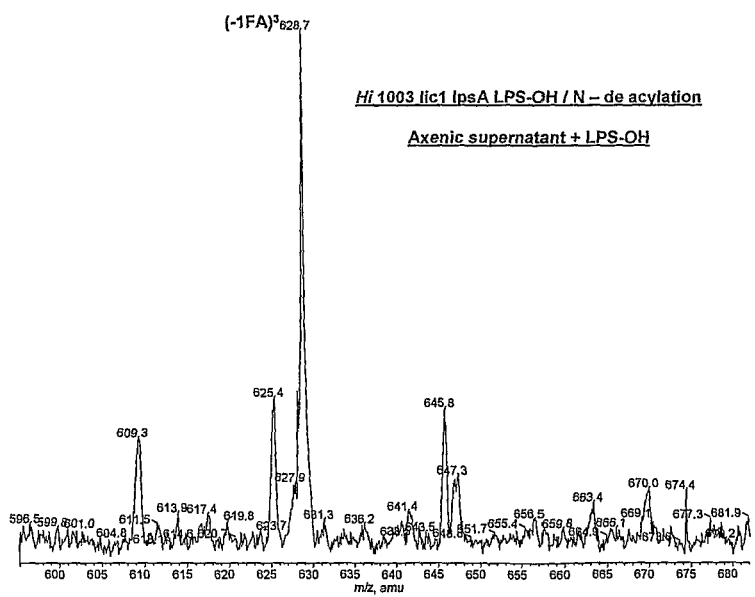
FIG. 33 is the CE-MS spectrum of *Haemophilus influenzae* strain 1003 lic1lpsA O-deacylated LPS, after treatment with isolated *Dictyostelium discoideum* amidases following growth of *Dictyostelium axenically*
Figure 34:
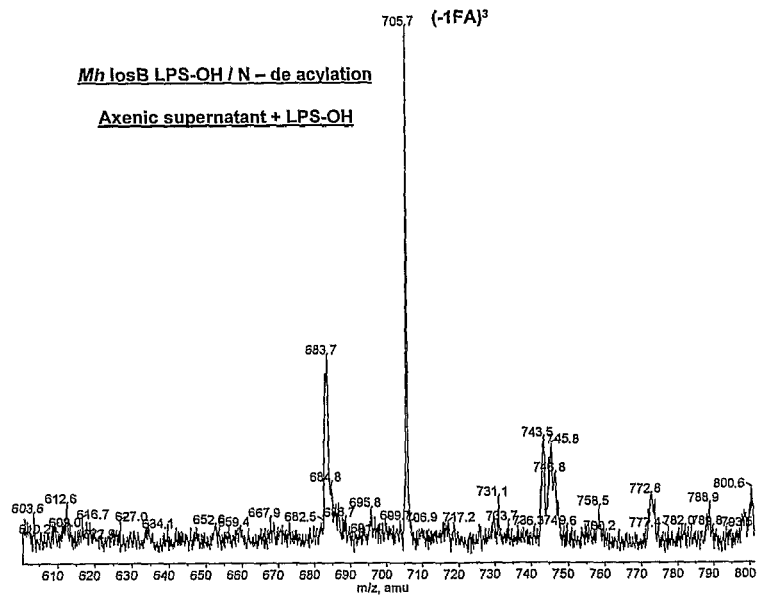
FIG. 34 is the CE-MS spectrum of *Mannheimia haemolytica* strain losB O-deacylated LPS, after treatment with isolated *Dictyostelium discoideum* amidases following growth of *Dictyostelium axenically*

We used this secreted amidase to N-deacylate LPS-OH. To utilise the amidase secreted during starvation of Dictyostelium, 5×10$^7$ cells/ml were starved for 16 hrs in Sorensen's buffer (2 mM Na$_2$HPO$_4$.2H$_2$O and 14.6 mM KH$_2$PO$_4$, pH 6.0) and the supernatant containing the secreted enzymes was collected by spinning down the cells at 2000 rpm for 2 min and the supernatant was incubated with the substrate LPS-OH (1 mg/ml), and the de-N-acylated product was isolated and identified by CE-MS from the Gram-negative bacteria Neisseria meningitidis immunotype L3 galE mutant (FIG. 29), Haemophilus influenzae lic1 lpt6 mutant (FIG. 30) and Mannheimia haemolytica losB mutant (FIG. 31). Similarly Dictyostelium has been found to secrete amidases when grown axenically. Therefore to utilise the amidase secreted during axenic growth, Dictyostelium cells were separated from axenic culture (AX2 medium) grown at a cell density of 3×10$^6$ cells/ml and the culture supernatant was used as the enzyme source with LPS-OH from Gram negative bacterial species. N-deacylation was confirmed by CE-MS analysis of the products from incubation of the axenic supernatant with Neisseria meningitidis immunotype L3 galE mutant (FIG. 32), Haemophilus influenzae lic1 lpt6 mutant (FIG. 33) and Mannheimia haemolytica losB mutant (FIG. 34). The advantages of these methods are the absence of Klebsiella aerogenes derived molecules in the supernatant.

Example 9

Figure 35:
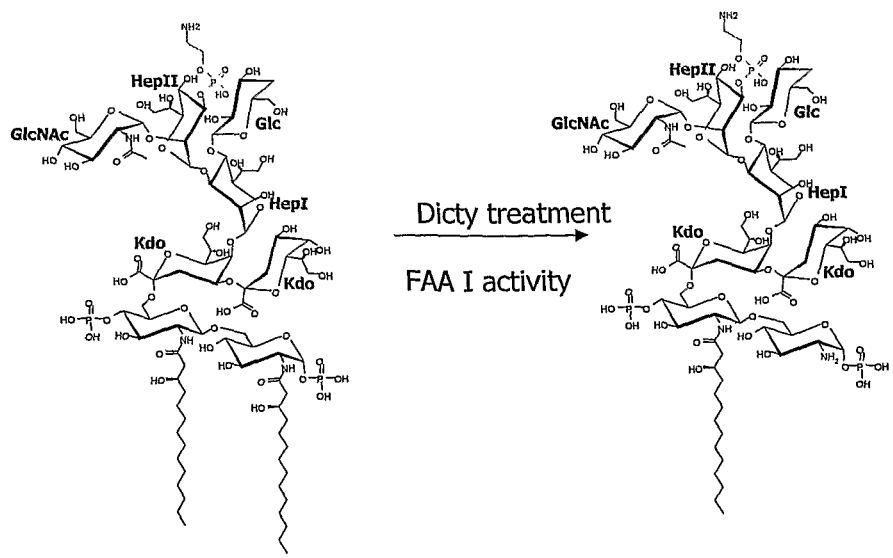
FIG. 35 is a schematic of isolated fatty acid amidase I activity on *Neisseria meningitidis* strain L3 galE O-deacylated LPS.
Figure 36:
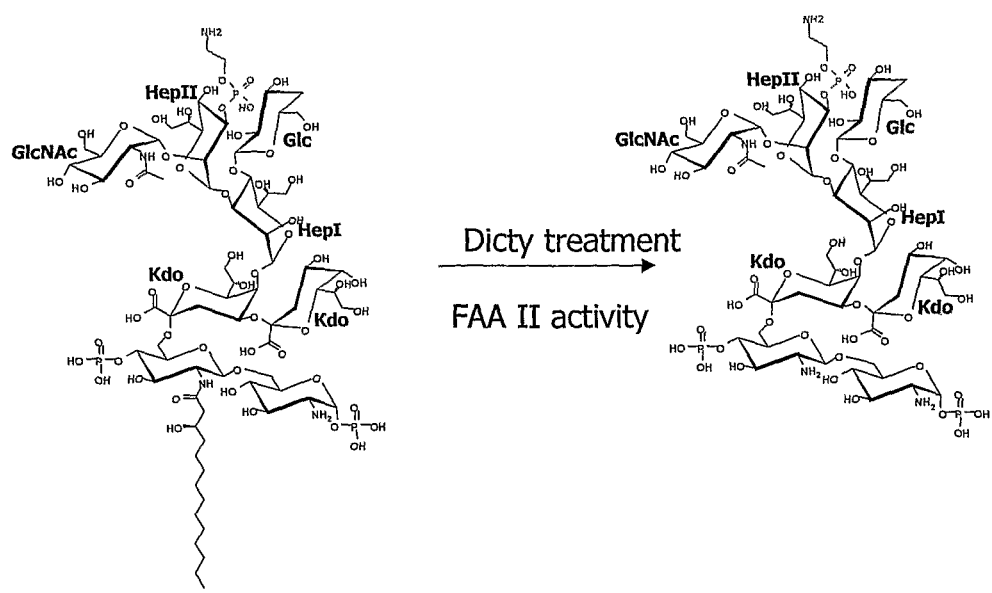
FIG. 36 is a schematic of isolated fatty acid amidase II activity on *Neisseria meningitidis* strain L3 galE mono-N-deacylated, O-deacylated LPS.

Production of a Glycoconjugate Utilising L3 galE O-Deacylated LPS Following Treatment Via the Dictyostelium discoideum/Klebsiella aerogenes Methodology Glycoconjugates with O-deacylated LPS and completely deacylated LPS derived from Neisseria meningitidis were produced in previous studies from our group [Cox et al, 2005]. The studies with O-deacylated LPS illustrated the proof-in-principle of using LPS derived glycoconjugates to induce a protective immune response against meningococcal disease; however, due to the hydrophobic nature of the O-deacylated LPS these conjugates were difficult to construct and characterise. Subsequently glycoconjugates were produced with completely deacylated LPS which were much more amenable to the manipulations involved in the production of the glycoconjugate, but did not contain crucial immunogenic epitopes in the core oligosaccharide due to losses during the harsh chemical conditions utilised to completely deacylate the LPS molecule. For this reason conjugates derived by this latter method did not induce a protective immune response to the majority of wild-type strains. A new strategy was therefore adopted which involves enzymic removal of the at least one N-linked fatty acid with the FAAI enzyme from Dictyostelium discoideum which enables retention of the immunogenic core oligosaccharide epitopes in a water-soluble molecule that is amenable to the several manipulations involved in conjugate production (FIGS. 35 & 36).

Step 1: LPS-OH Preparation

Figure 37:
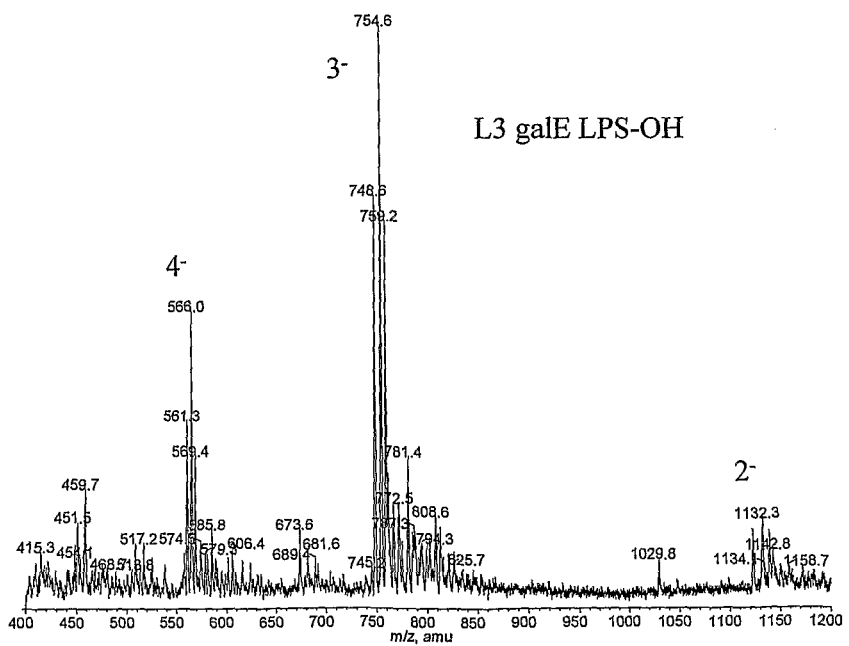
FIG. 37 is the CE-MS spectrum of *Neisseria meningitidis* strain L3 galE O-deacylated LPS, prior to treatment with isolated *Dictyostelium discoideum* amidases.

LPS was prepared from Neisseria meningitidis strain MC58 (#5) immunotype L3 galE mutant by standard methods. This LPS was then O-deacylated to produce LPS-OH by treatment at 37° C. with anhydrous hydrazine for 1 h. LPS-OH was quality controlled by sugar analysis and CE-ES-MS (FIG. 37).

Step 2: Dictyostelium discoideum Degradation of LPS-OH

Figure 38A:
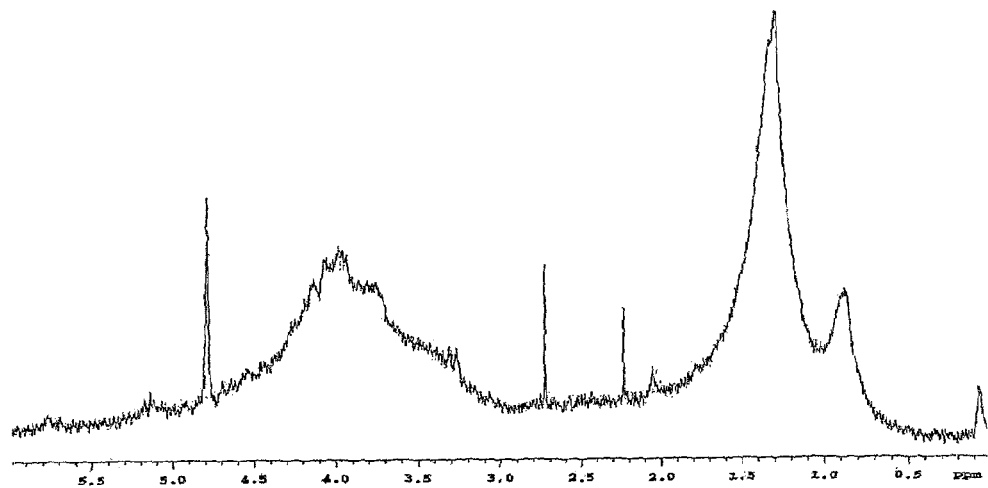
FIG. 38a is the $^1$H-NMR spectrum of *Neisseria meningitidis* strain L3 galE O-deacylated LPS before treatment with *Dictyostelium discoideum* amidase.
Figure 38B:
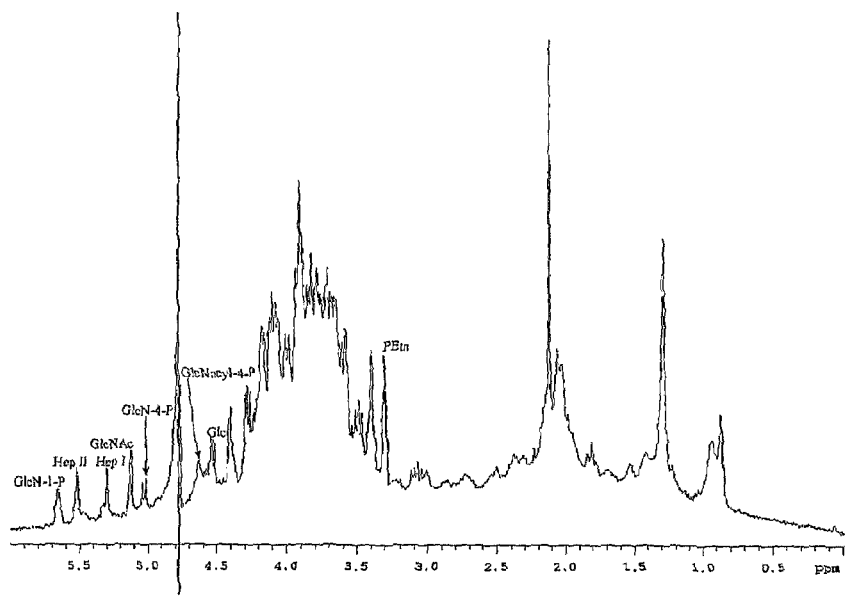
FIG. 38b is the $^1$H-NMR spectrum of *Neisseria meningitidis* strain L3 galE O-deacylated LPS after treatment with *Dictyostelium discoideum* amidase.

Dictyostelium discoideum cells were prepared as described above and added in the appropriate ratio to killed Klebsiella aerogenes cells as described above. LPS-OH was added to this suspension and left at 22° C. for 24 h. The suspension was pelleted by centrifugation at 10,000 g and the supernatant was purified on a spin column (Amicon) with a 10 kDa cut off membrane. Two water washes were also collected. The flow through material was then lyophilised, re-dissolved in water and applied to a Sephadex G-25 column and eluted with water. The resulting carbohydrate fractions were pooled and lyophilised. The resulting material was examined by CE-ES-MS (FIG. 24). The starting material before and the product after treatment with the isolated amidase were examined by NMR, and gave spectra consistent with the aggregative nature of the starting material (FIG. 38a) and the water-soluble nature of the product (FIG. 38b).

Figure 39:
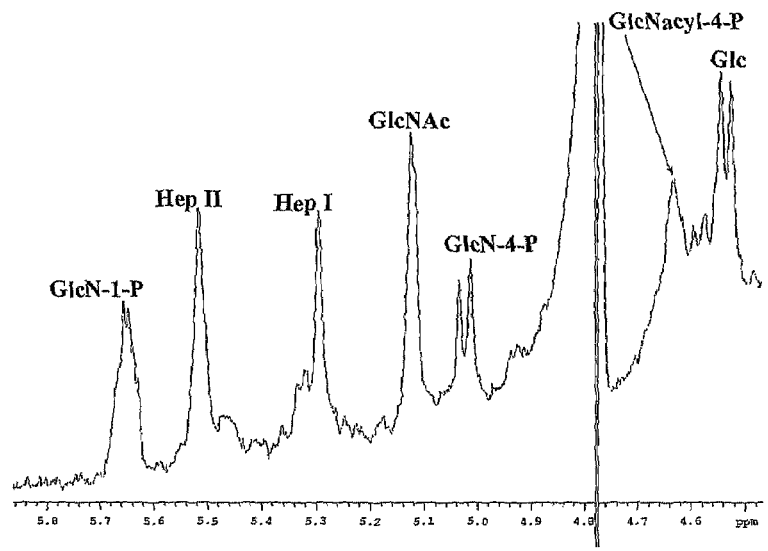
FIG. 39 is an expanded view of a region of FIG. 38b.
Figure 40:
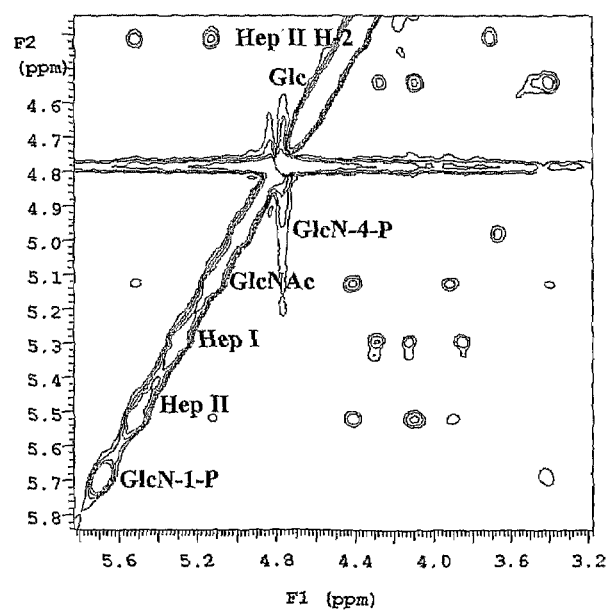
FIG. 40 is the $^1$H-NMR 2D-NOESY spectrum of *Neisseria meningitidis* strain L3 galE O-deacylated LPS after treatment with *Dictyostelium discoideum* amidase.
Figure 41:
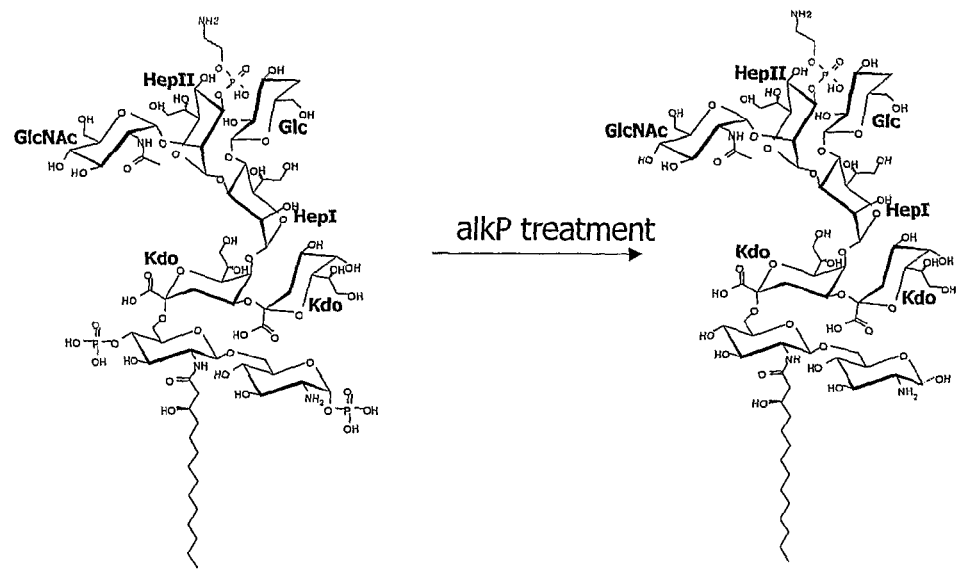
FIG. 41 is a schematic representation of the alkaline phosphatase de-phosphorylation step of the conjugation reaction scheme.
Figure 42:
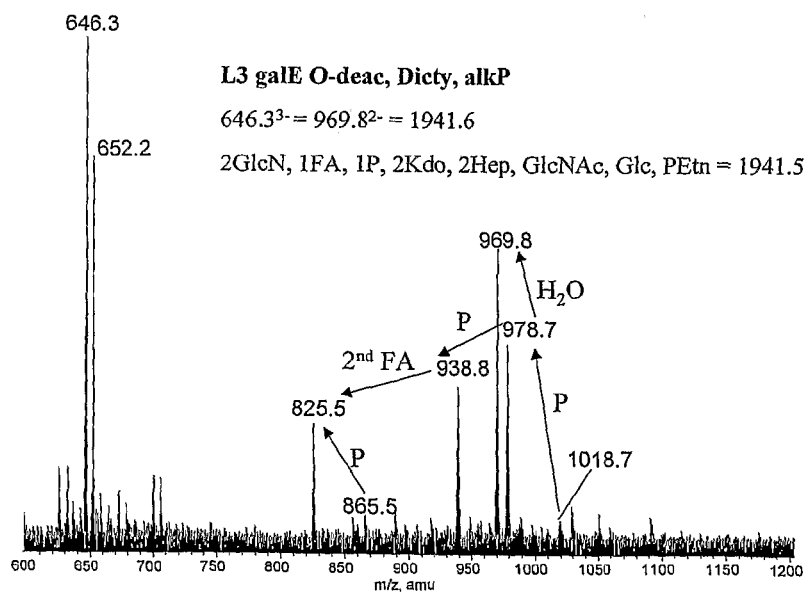
FIG. 42 is the CE-MS spectrum of *Neisseria meningitidis* strain L3 galE O-deacylated LPS, after treatment with isolated *Dictyostelium discoideum* amidases and alkaline phosphatase.
Figure 43:
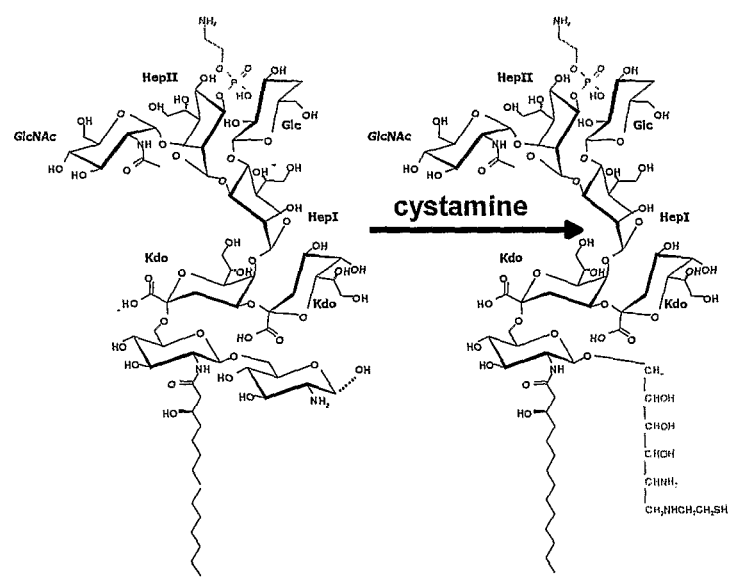
FIG. 43 is a schematic representation of the cystamine linker incorporation step of the conjugation reaction scheme.
Figure 44:
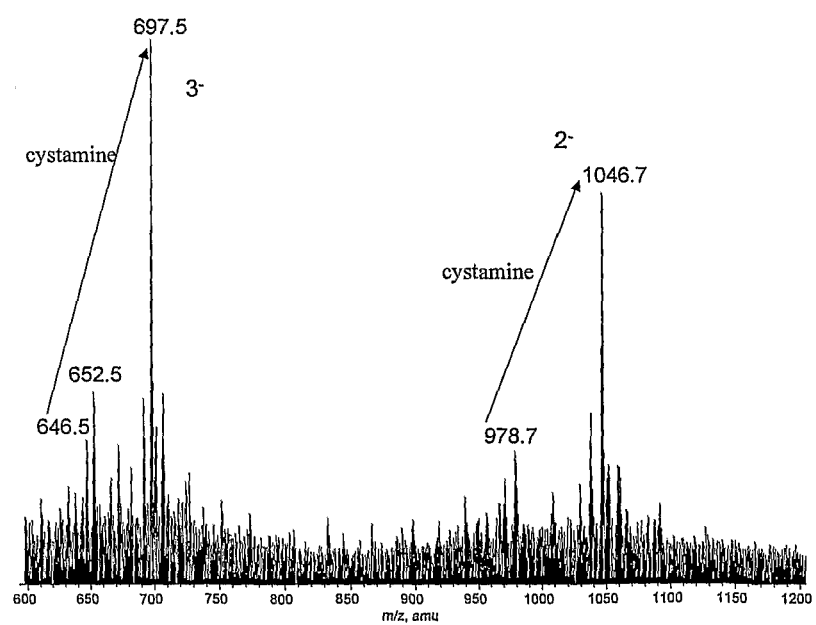
FIG. 44 is the CE-MS spectrum of *Neisseria meningitidis* strain L3 galE O-deacylated LPS, after treatment with isolated *Dictyostelium discoideum* amidases and incorporation of cystamine linker.
Figure 45A:
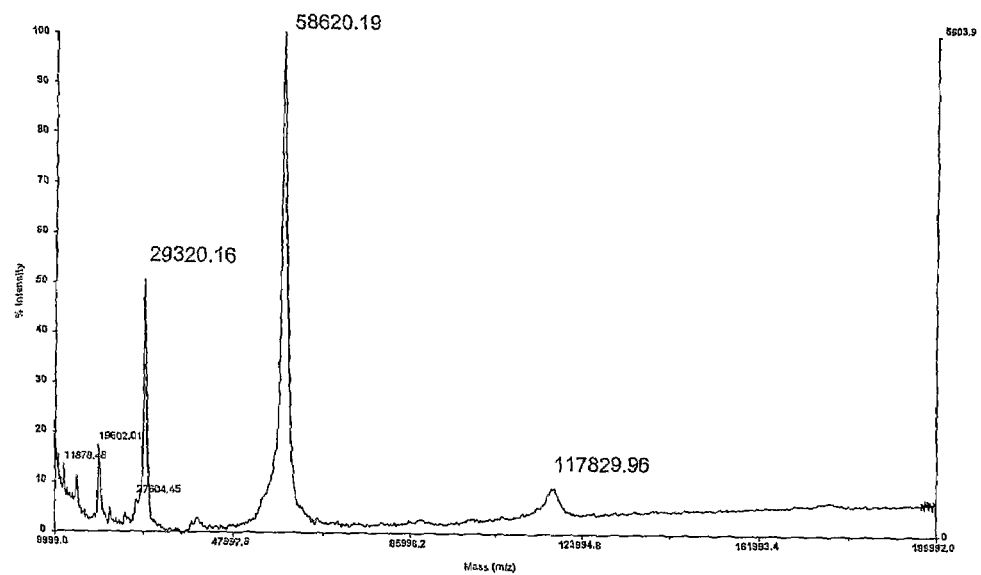
FIG. 45a is the MALDI-MS spectrum of CRM$_{197}$ protein
Figure 45B:
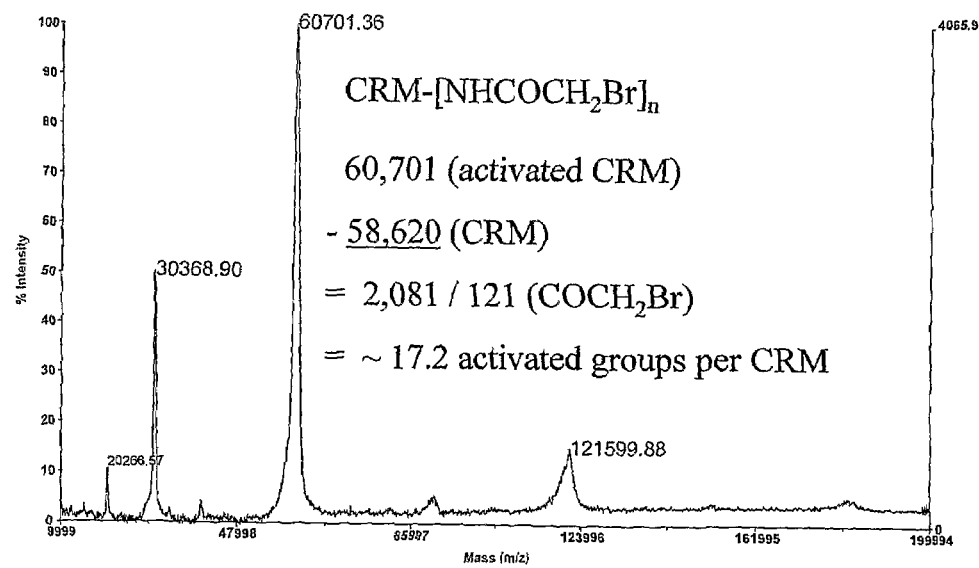
FIG. 45b is the MALDI-MS spectrum of CRM$_{197}$ protein following bromo-acetyl activation
Figure 46:
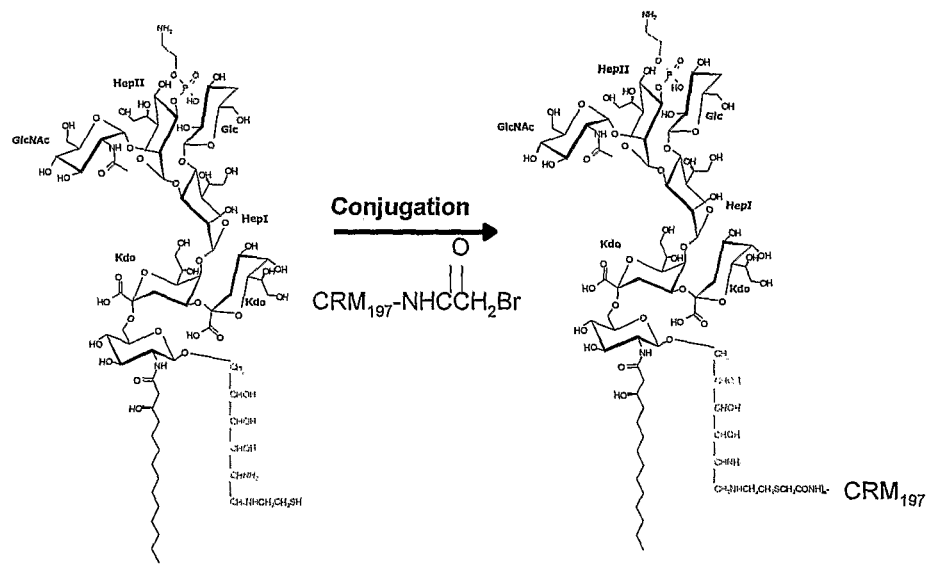
FIG. 46 is the schematic representation of the conjugation step of the conjugation reaction scheme.
Figure 47:
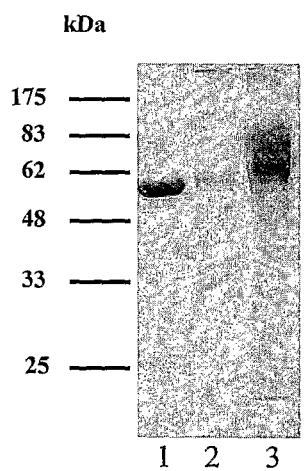
FIG. 47 is an SDS-PAGE analysis of CRM$_{197}$ (Lane 2), bromo-acetylated CRM$_{197}$ (Lane 3), conjugate (Lane 4), molecular weight ladder (Lane 1).
Figure 48:
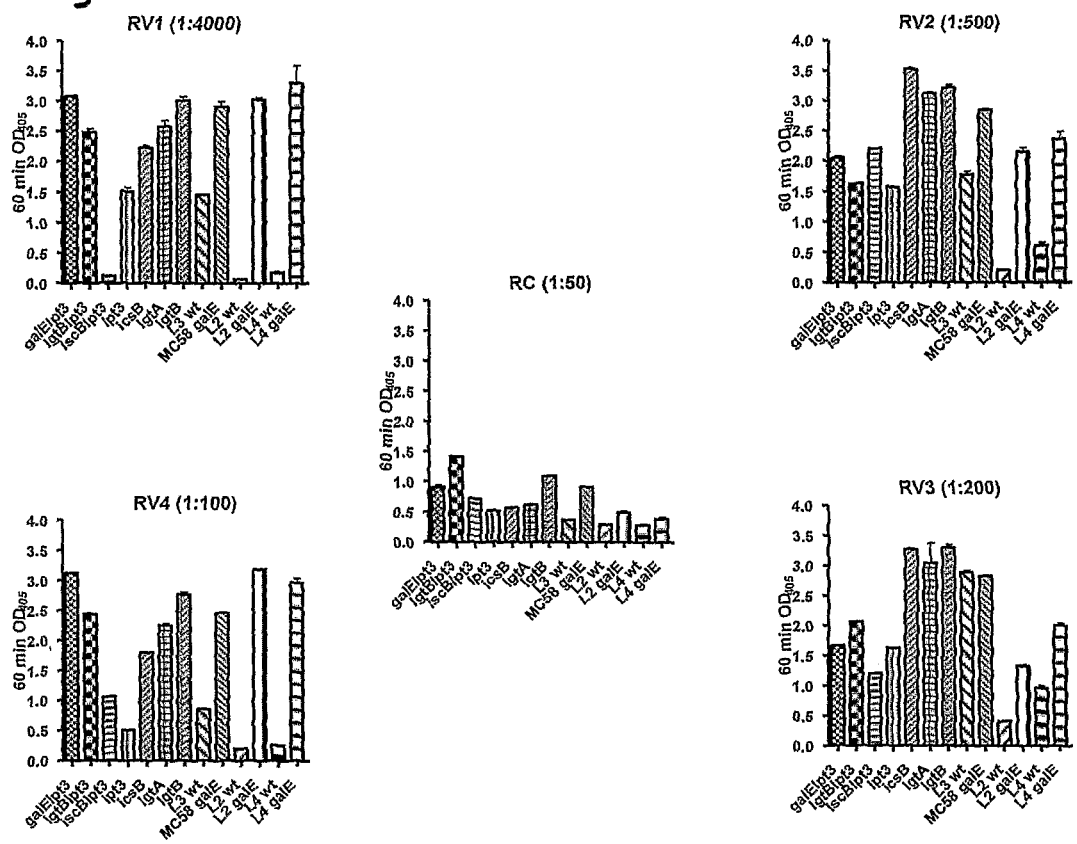
FIG. 48 is an ELISA of post-immune rabbit sera against purified LPS from *N. meningitidis* as indicated.

A well-resolved spectrum was obtained consistent with a water-soluble molecule being produced following removal of at least one N-linked fatty acid. Examination of the anomeric region of the $^1$H-NMR spectrum reinforces this (FIG. 39). Additionally the anomeric region of the 2D NOESY spectrum (FIG. 40) illustrates NOE connectivities consistent with the LPS-OH and core OS molecules confirming that the conformation of the potentially immunogenic oligosaccharide region has been retained in this procedure.

Step 3: Alkaline Phosphatase Treatment of *Dictyostelium discoideum* Treated LPS-OH ~38 mg of *Dictyostelium discoideum* treated LPS-OH was treated with recombinant alk. P (Roche; 700 U/ml at t=0, 700 U/ml at t=6 h) for 30 h at 37° C. in order to remove the mono-phosphate esters as illustrated in FIG. 41.

The mixture was boiled to denature the phosphatase and centrifuged (10,000 g, 15 min.) and the supernatant was applied to a Sephadex G-25 column and eluted with water. The resulting carbohydrate fractions were pooled and lyophilised. The resulting material was examined by CE-ES-MS (FIG. 42).

The doubly charged ion at m/z $1018.7^{2-}$ for the mono-N-acylated substrate has clearly lost either one or two phosphate residues. The completely deacylated substrate has lost both phosphate residues to give the doubly charged ion m/z $825.5^{2-}$.

Step 4: Attachment of Cystamine Linker to *Neisseria meningitidis* galE *Dictyostelium discoideum*/alkP Product In order to link the Nm galE *Dictyostelium discoideum*/alkP product to a carrier protein to construct the glycoconjugate it was necessary to attach a linker molecule. Cystamine was used for this purpose, as this linker utilises sulphur chemistry to attach to the carrier protein and does not involve utilising amino groups so that the potentially immunogenic phosphoethanolamine moiety would not be modified during the conjugation reaction. In order to ensure that the cystamine linker is attached to the aldehydro group created by the alkaline phosphatase treatment and avoid cross-linking of the carbohydrate molecules a large excess of cystamine was reacted with the carbohydrate moiety, according to FIG. 43.

~25 mg of the *Neisseria meningitidis* galE Dicty/alkP product was reacted with a 30× molar excess of cystamine at 37° C. for 72 h in a solution of 0.1 M $NaHCO_3$, pH 8.4. The reaction mixture was then applied to a Sephadex G-25 column and eluted with water. The resulting carbohydrate fractions were pooled and lyophilised. The resulting material was reduced with 200 mM DTT in 0.1M $NaHPO_4$ at pH 8.1 for 1 h at room temperature. The reaction mixture was then applied to a Sephadex G-25 column and eluted with water. The resulting carbohydrate fractions were pooled and lyophilised and examined by CE-ES-MS (FIG. 44).

The doubly charged ion at m/z $1046.7^{2-}$ and the triply charged ion at m/z $697.5^{3-}$ are consistent with the addition of the cystamine to the carbohydrate molecule.

Step 5: Activation of the Protein Carrier

In order to conjugate the protein carrier molecule $CRM_{197}$ to the cystamine-tagged carbohydrate it was necessary to modify the amino groups on the $CRM_{197}$ protein by treatment with N-succinimidyl-bromo-acetate. This was achieved by mixing $CRM_{197}$ (30 mg) in 0.1 M $NaHPO_4$, 1 mM EDTA, 0.02% sodium azide, pH 7.1 cooled to 4° C., with N-succinimidyl-bromo-acetate (22 mg in 100 μl DMF) at room temperature for 2.0 h. The reaction mixture was then applied to a Sephadex G-25 column and eluted with 0.1 M $NaHPO_4$, 5 mM EDTA, 0.02% sodium azide, pH 6.0 and stored at 4° C. until used. As shown in the two MALDI spectra (FIG. 45*ab*) it can be determined that approximately 17 amino groups on the lysine residues of $CRM_{197}$ were modified by this procedure.

Step 6: Conjugation of Cystamine Tagged CHO to the Activated Protein Carrier

In order to conjugate the cystamine-tagged carbohydrate molecule to the activated protein carrier ~15 mg of activated $CRM_{197}$ was added to ~18 mg of carbohydrate and left at room temperature for 17 h as illustrated in FIG. 46.

The reaction was cooled to 4° C. and then an excess of cysteine (~50 mg) was added in order to cap any free bromo-acetate groups that may be remaining following the conjugation reaction.

The reaction mixture was then purified on a Sepharose 6B column eluting in PBS/10 mM citrate. The material was concentrated on an ultra-15 spin column and quantified for protein and carbohydrate giving a ratio of ~11 CHO molecules per protein.

The conjugate was examined by SDS-PAGE (FIG. 47) and Coomassie staining, revealing a migration pattern consistent with the carbohydrate to protein ratio The conjugate was also examined by Western blot using a monoclonal antibody (mAb B5) specific for an inner core oligosaccharide epitope. The conjugate was recognised by this mAb indicating that the conjugation process had not compromised the conformation of the inner core and therefore the inner core epitopes were appropriately presented in this glycoconjugate.

Example 10

Immunogenicity of Glycoconjugate

The glycoconjugate was used to immunise four rabbits (3 injections of 50 μg of conjugated carbohydrate per injection three weeks apart) and the immune response monitored by LPS ELISA for strength and degree of cross-reactivity, as illustrated in FIG. 48, good titres and excellent cross-reactivity was observed, with LPS that contains a PEtn moiety at the 3-position of Hep II being recognised. Additionally glycoforms that are extended from Hep I were also recognised. The specificity of the immune response was indicated, as extended glycoforms with PEtn at the 6-position (e.g. L2 and L4 wt) were not recognised. Control sera from a rabbit that received non-conjugated CRM and carbohydrate did not as expected give a specific cross-reactive immune response.

The sera was examined for functional activity in a bactericidal assay and illustrated efficient killing of the homologous strain and some killing of the wt strain when compared to the corresponding pre-immune sera (FIG. 49).

Example 11

Production of Dd1 and Dd2 Specific Knockout Mutants in *Dictyostelium*

Standard mutagenesis strategies are adopted to make FAAHI and FAAHII independent knockout mutants. The mutant is used in specific N-deacylation reactions of LPS-OH from Gram-negative bacteria when grown vegetatively, which guarantee the removal of specific fatty acid to create a defined mono-acylated molecule.

Generation of FAAHI Knock Out Mutant

Neomycin resistance gene cassette or Blasticidin resistance gene cassette is introduced at the SspI site of Dd1 gene cloned in pCR2.1 vector (Invitrogen), the recombinant DNA obtained is transformed into *Dictyostelium* to generate knockout cells by homologous recombination.

Generation of FAAHII Knock Out Mutant

Neomycin resistance gene cassette or Blasticidin resistance gene cassette is introduced at the EcoRV site of Dd2 gene cloned in pCR2.1 vector (Invitrogen), the recombinant DNA obtained is transformed into *Dictyostelium* to generate knockout cells by homologous recombination.

While the preferred embodiments of the invention have been described above, it will be recognized and understood that various modifications may be made therein, and the appended claims are intended to cover all such modifications which may fall within the spirit and scope of the invention.

REFERENCES

Cox, A. D. et al Vaccine, 2005, 23, 5045-5054
Verret, C. R. et al Rev. Infect. Dis, 1984, 6, 452-454

The invention claimed is:

1. A method of preparing a vaccine comprising a conjugate, the method comprising:
   separating lipopolysaccharide from a bacterium of interest, wherein the bacterium is not a substrate for growth of *D. discoideum* and said bacterium is selected from the group consisting of *Neisseria meningitidis* and *Mannheimia haemolytica*;
   detoxifying the lipopolysaccharide by de-esterfying the lipopolysaccharide;
   removing at least one N-linked fatty acid from the lipopolysaccharide with an isolated fatty acid amidase comprising a peptide having the amino acid sequence as set forth in either SEQ ID No:1 or SEQ ID No: 2; and
   conjugating the modified lipopolysaccharide to a suitable carrier molecule.

2. A method of recovering a modified lipopolysaccharide (LPS) from a bacterium of interest comprising:
   separating lipopolysaccharide from the bacterium of interest, wherein the bacterium is not a substrate for growth of *D. discoideum* and said bacterium is selected from the group consisting of *Neisseria meningitidis* and *Mannheimia haemolytica*;
   detoxifying the lipopolysaccharide by de-esterfying the lipopolysaccharide layer;
   removing at least one N-linked fatty acid from the lipopolysaccharide with an isolated fatty acid amidase comprising a peptide having the amino acid sequence as set forth in either SEQ ID NO:1 or SEQ ID NO: 2; and
   recovering the modified LPS.

3. The method according to claim 2 wherein the modified LPS is water-soluble, O-deacylated and has at least one of the two N-linked fatty acids removed.

* * * * *

SEQUENCE LISTING

```
<160> NUMBER OF SEQ ID NOS: 14

<210> SEQ ID NO 1
<211> LENGTH: 550
<212> TYPE: PRT
<213> ORGANISM: Dictyostelium discoideum

<400> SEQUENCE: 1

Met Asn Arg Leu Thr Asn Ile Ser Lys Ile Arg Lys Ser Leu Ile Asp
1               5                   10                  15

Gly Lys Leu Lys Val Asn Asp Leu Val Leu Asn Lys Ile Lys Glu Ile
            20                  25                  30

Asn Lys Val Ser Pro Asn His Leu Asn Thr Phe Ile Ser Leu Gln Asp
        35                  40                  45

Glu Lys Ser Leu Gly Lys Gln Ile Lys Glu Ser Gln Glu Arg Tyr Asp
    50                  55                  60

Asn Gly Thr Asn Lys Arg Leu Asp Gly Ile Pro Ile Gly Val Lys Asp
65                  70                  75                  80

Asn Phe Ser Ser Lys Asn Phe Lys Thr Thr Cys Gly Ser Lys Ile Leu
                85                  90                  95

Glu Asn Tyr Ile Pro Ser Phe Asp Ser Thr Val Val Lys Leu Leu Lys
            100                 105                 110

Glu Glu Gly Ala Ile Ile Ile Gly Lys Thr Asn Met Asp Glu Phe Ser
        115                 120                 125

Met Gly Ser Ser Ser Thr Ser Gly His Phe Gly Lys Val Ile Asn Pro
    130                 135                 140

Trp Ser Lys Pro Asn Asn Asn Asn Asn Asn Asp Asn Asp Asn Asn Asn
145                 150                 155                 160

Asn Gly Glu Val Leu Tyr Val Ala Gly Gly Ser Ser Gly Gly Ser Ala
                165                 170                 175

Ala Ala Val Ala Ser Asn Tyr Cys Val Ala Ser Ile Gly Ser Asp Thr
            180                 185                 190

Gly Gly Ser Ile Arg Gln Pro Ser Ser Tyr Cys Gly Val Val Gly Phe
        195                 200                 205

Lys Pro Ser Tyr Gly Leu Ile Ser Arg Phe Gly Leu Val Ala Tyr Ala
    210                 215                 220

Ser Ser Leu Asp Thr Pro Gly Val Leu Thr Asn Asn Val Glu Asp Ala
225                 230                 235                 240

Ala Glu Leu Leu Asp Ile Leu Ile Lys Lys Asp Gln Glu Asn Asp Ser
                245                 250                 255

Thr Ser Ile Glu Phe Ile Asn Asn Asn Gln Asn Gln Asn Gln Asn Asn
            260                 265                 270

Gly Glu Lys Arg Asn Ile Leu Asp Glu Phe Asn Glu Lys Leu Lys Asn
```

```
                     275                 280                 285
Lys Asn Ile Lys Asp Leu Val Phe Gly Ile Pro Lys Asp Tyr Leu Val
        290                 295                 300
Lys Glu Leu Asp Thr Asp Ile Leu Asn Leu Trp Lys Glu Val Val Glu
305                 310                 315                 320
Glu Ile Glu Lys Arg Gly Gly Lys Val Val Ser Val Ser Leu Pro His
                325                 330                 335
Thr Arg Tyr Ala Leu Pro Ala Tyr Tyr Leu Leu Ala Thr Ser Glu Ala
                340                 345                 350
Ser Ser Asn Leu Ser Arg Phe Asp Gly Val Arg Tyr Gly Tyr Arg Phe
                355                 360                 365
Glu Glu Glu Lys Asp Glu Asn Lys Val Asp Asn Asp Asp Asp Asp Asp
        370                 375                 380
Asp Asp Val Asp Glu Asn Lys Ile Gly Met Gly Leu Lys Asp Met Tyr
385                 390                 395                 400
Thr Lys Thr Arg Thr Asn Gly Phe Gly Glu Glu Val Lys Lys Arg Ile
                405                 410                 415
Ile Leu Gly Thr Met Ala Leu Ser Arg Ser Ser Tyr Asp Asn Phe Tyr
                420                 425                 430
Thr Lys Ala Gln Lys Ile Arg Arg Leu Val Ser Asp Asp Phe Lys Asn
        435                 440                 445
Val Phe Gln Gly Glu Asn Lys Val Asp Ile Leu Ile Thr Pro Thr Ala
450                 455                 460
Pro Ser Pro Ala Phe Lys Gln Asn Glu Lys Met Asp Pro Ile Glu Val
465                 470                 475                 480
Tyr Val Asn Asp Ile Met Thr Ile Pro Ser Asn Leu Ala Gly Leu Pro
                485                 490                 495
Ala Cys Ser Ile Pro Leu Lys Leu Ser Asn Ser Asn Leu Pro Ile Ser
                500                 505                 510
Val Gln Leu Ile Ser Asn Arg Leu Thr Asp Asp Asn Leu Leu Phe Ala
                515                 520                 525
Ala His Thr Ile Met Asn Phe Asp Cys Tyr Lys Asp Phe Thr Ser Leu
        530                 535                 540
Thr Pro Asn Tyr Leu Lys
545                 550

<210> SEQ ID NO 2
<211> LENGTH: 637
<212> TYPE: PRT
<213> ORGANISM: Dictyostelium discoideum

<400> SEQUENCE: 2

Met Thr Ser Ser Ser Leu Ser Lys Ser Ser Thr Ser Ser Thr Ser
1               5                   10                  15
Ser Lys Asn Glu Glu Lys Gly Glu Lys Lys Ile Tyr Asp Leu Ile Ser
                20                  25                  30
Leu Glu Val Pro Arg Leu Gln Gly Leu Leu Leu Arg Ser Thr Leu Phe
            35                  40                  45
Leu Cys Glu Asn His Tyr Leu Lys Asn Ser Phe Leu Ser Ser Leu Tyr
        50                  55                  60
Thr Lys Asn Lys Met Pro Leu Ile Ser Gln Phe Asn Leu Asn Leu Ser
65                  70                  75                  80
Pro Thr Phe Tyr Pro Ile Val Asp Ile Ser Asn His Gln Gln Gln Gln
                85                  90                  95
```

-continued

```
Gln Asn Lys Ser Glu Phe Thr Phe Lys Lys Tyr Leu Ala Thr Asp Met
                100                 105                 110

Leu His Asp Lys Asp Leu Ile Lys Tyr Leu Gln Ser Lys Asn Leu Glu
            115                 120                 125

Ile Asn Ser Gln Ser Ser Ser Ser Ser Ser Asn Asn Gln Ser Leu
        130                 135                 140

Ile Asn Asn Ile Pro Glu Asn Ser Ile Ile Asn Tyr Asn Leu Tyr
145                 150                 155                 160

Met Thr Gly Lys Ile Thr Pro Asn Glu Ile Ala Asn Phe Phe Ile Glu
                165                 170                 175

Cys Lys Asn His Ser Asp Glu Gln Ser Pro Leu Lys Ala Phe Ile
            180                 185                 190

Lys Ile Leu Glu Asp Asp Ile Lys Ser Gln Ala Met Ala Ser Ala Glu
            195                 200                 205

Arg Trp Lys Ser Gly Ser Pro Leu Ser Leu Ile Asp Gly Val Pro Ile
            210                 215                 220

Ser Leu Lys Asp Glu Ile Asp Gln Ile Gly Tyr His Thr Thr Cys Gly
225                 230                 235                 240

Thr Thr Phe Leu Glu Lys Val Phe Pro Asn Val Lys Thr Glu Asp Ser
                245                 250                 255

Gly Val Ala Lys Met Leu Arg Gln Gln Gly Ala Ile Leu Val Gly Lys
            260                 265                 270

Asn Asn Met His Glu Ile Gly Ile Ser Thr Leu Gly Tyr Asn Thr His
            275                 280                 285

Phe Gly Phe Thr Arg Asn Pro Tyr Asn Leu Asn His Tyr Pro Gly Gly
        290                 295                 300

Ser Ser Ser Gly Ser Ala Ser Ser Val Ser Ala Gly Leu Asn Pro Leu
305                 310                 315                 320

Ser Ile Gly Cys Asp Gly Gly Ser Ile Arg Val Pro Ala Ser Leu
                325                 330                 335

Cys Gly Val Val Gly Leu Lys Pro Thr Phe Ala Arg Val Ser His Gly
            340                 345                 350

Gly Ile Phe Asp Leu Cys Trp Ser Val Gly His Val Gly Pro Ile Gly
        355                 360                 365

Ser Ser Val Ile Asp Thr Ala Ile Gly Tyr Ala Cys Ile Ala Gly Ser
370                 375                 380

Asp Ser Ala Asp His Gln Ser Val Leu Ala Glu Gln Tyr Gly Gly Lys
385                 390                 395                 400

Pro Thr Val Pro Met Phe Thr Glu Ile Pro Leu Ile Gln Pro Leu Lys
                405                 410                 415

Gly Leu Lys Ile Gly Val Phe Tyr Asp Trp Ile Asn Asp Cys Asn Ile
            420                 425                 430

Glu Phe Lys Asp Ser Thr Tyr Lys Cys Ile Glu Ile Leu Lys Glu Gln
            435                 440                 445

Gly Ala Glu Ile Ile Glu Ile Glu Ile Ser Asn Leu Leu Val Thr Arg
        450                 455                 460

Leu Ser Gln Gly Ala Ile Ile Leu Ser Glu Met Asn Ser Ser Met Lys
465                 470                 475                 480

Arg Phe Lys Asn Tyr Ser Asn Glu Leu Gln Tyr Asp Ser Arg Ile Ser
                485                 490                 495

Leu Ser Ile Gly Asn Ile Leu Pro Thr Ser Asp Tyr Leu Gln Ala Asn
            500                 505                 510

Lys Val Arg Thr Phe Cys Ile Glu Gln Phe Thr Glu Ile Phe Lys Gly
```

```
                515                 520                 525
Val Asp Leu Ile Val Thr Pro Thr Asn Ala Ile Ala Ala Pro Glu Ile
            530                 535                 540

Glu Lys Ser Val Leu Ser Met Gly Glu Ser Asn Phe Gly Ser Val Gly
545                 550                 555                 560

Glu Leu Met Lys Tyr Val Phe Ile Gly Asn Ile Thr Gly Ile Pro Gly
                565                 570                 575

Ile Thr Val Pro Val Gly Leu Thr Lys Asp Lys Asn Leu Pro Ile Gly
            580                 585                 590

Phe Gln Ile Met Ala Lys Trp Trp Gln Glu Asp Leu Leu Leu Tyr Thr
                595                 600                 605

Ser Tyr Val Leu Glu Lys Asn Ile Asp Phe Lys Gly Lys Pro Gln Tyr
            610                 615                 620

Tyr Asn Cys Pro Leu Thr Asn Cys Thr Asn Pro Asn Asn
625                 630                 635

<210> SEQ ID NO 3
<211> LENGTH: 3653
<212> TYPE: DNA
<213> ORGANISM: Dictyostelium discoideum

<400> SEQUENCE: 3
atgtatagat tctaaatgtc aattatatgg tattgaacgt agtgaatata ttacttgtat      60
cgattattat aattgtccag gtccaaatac atgtgcttca ttaggttttg ataatggaaa     120
ttacatttca aaatgtgtgc ctttaaaacc attaaaaagt gattgtaaaa ctcaatcaga     180
atgtttcatt ggtggtatat gttcaagtga aaataaatgt atttcaagat attcaaagaa     240
actaaatgaa aattgtttat ataatagtga atgtgatttt ggattaaaag taagtaaaaa     300
aaaaaaaaaa aaaaaaaaaa aaaaaaaaaa aaaaaaaaaa aaaaaaaaaa aaaaaaaaaa     360
aaaaaattaa tttaacaaat aataactcct attttttacca atacaataag tgtgaaacta     420
caatttatca ttattttcca aatggtacat ttaaaaattt tgaagaaatt aataaatgtg     480
taccattgat ctattcaaaa acaacaaatt gtttagatga aggttgtcaa gaatatgaat     540
tttgtaatgg tgcaacaaat aaatgttatc ctaaaaagaa atacacaaat gattgtaaaa     600
aagcagaaaa agaaagagat tcatgctaca tttcaaataa ctgcttcttt tcaaatgaac     660
aatatgattt actatcttct gattctccat tttcaaatga aaattcttgt caaatgaaac     720
attgtaaatg tcaaacaatc aattattta accaatgtca aaatacatat acattttgtc     780
aataaaacct ttgataataa atatatatta aaatttcatt tttaccttat tataattttt     840 ttttttttt tcaattctcc cttaatatca cttttttta aaaaaaaaa aaaaaaaaa       900 aaaaatcaaa aaactcgttt aaacgacttt tttttaattt ttatttttt tattttatt       960 ttttatttt aattaaaaaa atcattgatg attaaaaacg atgaatagat taacaaatat    1020
atcaaaaatt agaaaatcat taatagatgg aaaattaaaa gtgaatgatt tagttttaaa    1080
taaaatcaaa gagattaata aagtttcacc aaatcattta aatacattta tttcacttca    1140
agatgagaaa tcattaggga aacaaattaa agagagtcaa gagagatatg ataatggtac    1200
aaataaaaga ttagatggta taccaattgg tgtaaaagat aatttctcaa gtaaaaattt    1260
taaaacaact tgtggttcaa agattttaga gaattatata ccaagttttg attcaactgt    1320
tgttaaatta ttaaaagagg aaggtgcaat aattattggt aaaactaata tggatgaatt    1380
ttcaatgggt tcatcttcaa cttctggtca ttttggtaaa gtaattaatc catggagtaa    1440
```

```
accaaataat aataataaca atgataatga taataataat aatggagagg tttatatgt    1500 tgcaggtggt tcatcaggtg gttcggcagc agcagttgct tcaaattatt gtgttgcatc    1560
aattggatca gatacaggtg gttcaattag acaaccatca tcatattgtg gtgttgttgg    1620
ttttaaacca tcctatggtt taatatcacg ttttggttta gttgcatatg cttcatcatt    1680
agatacacct ggtgttttaa ctaataatgt tgaagatgct gctgaattat tagatatttt    1740
aattaaaaaa gatcaagaaa atgattcaac ttcaattgaa tttataaata ataatcaaaa    1800
tcaaaatcaa aataatggtg aaaaaggaa tattttagat gaatttaatg aaaaattaaa    1860
aaataaaaat ataaaagatt tagtatttgg tataccaaaa gattatttag ttaaagaatt    1920
agatacagat atacttaacc tttggaaaga agttgttgaa gaaattgaaa aagaggtgg    1980 taaagttgta tcagttagtt taccacatac tcgttatgca ttaccagctt attatttatt    2040
agcaacatct gaagcaagtt caaacctttc aagatttgat ggtgttagat atggttatag    2100
atttgaagaa gaaaaagatg aaaataaagt agataatgat aatgatgatg atgatgatgt    2160
tgatgaaaat aaaattggta tgggattaaa agatatgtat acaaaaacta gaacaaatgg    2220
ttttggcgaa gaagttaaaa aagaattat acttggtaca atggcattat caagatcatc    2280
atatgataat ttctatacaa aagctcaaaa gattagaaga ttagtatcag atgatttaa    2340 aaatgttttc caaggtgaaa ataaagtaga tattttaata acaccaactg caccatctcc    2400
agcatttaaa caaaatgaaa aatggatcc aatcgaagtt tatgtaaatg atattatgac    2460
aataccttca aatttagcag gttaccagc atgttcaatt cctttaaaac tttcaaattc    2520
aaatttacca atttcagttc aactaatttc aaatcgttta actgatgata atttatattt    2580
tgcagctcat acaattatga attttgattg ttacaaagat tttacatcac ttacaccaaa    2640
ttatttaaaa taataaaata aaaattataa acactatagt gtttgtttat ttaaaaatta    2700
aatcttttat ataatttgtt ttatatttta tccaccattt atatttaaat aaaattaaaa    2760
ttattgtaat aataattata acaccaatta ttgaacaaac tattaaaatt attaaatcat    2820
tttttgataa attatttgat tgaaatgatt gtgaataatt gaatgatttt gaattcgatg    2880
atgataataa tgatgattta ctacaaactg tagtatcact atcagaatta ccacctaata    2940
aaaattgaaa atttggatca attattgctt tcttttaaa attgggaata ttaattgcaa    3000
cttgtattga tatttcttga gaatttatac ttttaaccaa cgaatttgga attattgaat    3060
ttgataataa aattttttta tcatcaataa taccttcctt tataaattca ccaaccattg    3120 aaattcatt aacccttaat acaatccatg ataaatttgt ttcatttaaa tttctatatc    3180
caaatgaatt tgaaatacat gtcgttttat catcgtcatt atattttaat gttgaattaa    3240
atataatttg taatgtattt aatggtgagc taaattgata atttaaaatt tcaattgaaa    3300
attttaatgt atttggttta acacttattg attcaccagc aaattctaaa attgttgata    3360
aatttgattg attttgaggg aattttgaaa ttataattt aatttcacta taaccatttt    3420
cagttgggaa tttatttgaa tacattattg atgttgcatt atattgattg aatgatgaat    3480
tttcataatt tttaaaaact ttccatggta attttgaaaa atcaaattct taacaatttt    3540
catttgaaaa accaacttca caactttaa aaaatgatat atcagcataa ccacctccac    3600
aattattatt attattatta ttatctgatt taatccattg ataagttgat ggt           3653
```

<210> SEQ ID NO 4
<211> LENGTH: 4300
<212> TYPE: DNA
<213> ORGANISM: Dictyostelium discoideum

<400> SEQUENCE: 4

```
gtagagaaca agaaacaaac aaaacaacaa atccaaataa ctctaaaaaa ttaaaaaatt      60
tcaaaaataa taatcattat tttattgtgt atatatatag aaaaaaaaaa aaaaaaaaaa     120
aaaaaaaaaa aaaaataaac taccaacctt tttattttt ttttttttc caaattttt       180
ttttttttct taaaattact aaaacattct ctattactta acatattaat taatcaatat     240
ttttaaaaaa aagttaaaat gttatttta ttaaaataga ttaataattg aaggaaaaaa     300
aaaaaaacca taaaataaaa taaaaatgat agatctaaat aaaataaacc tttcaaaaaa     360
actttatttt ttgaaattaa ttaaacacaa atttcttcca aaataaataa caatttata     420
tttttttgaca acattaatta aaaaggaaat aaatagtttt tttattttta ttatttttt      480
tttttttaggg caaagattaa taataatttt ccaatttttt caaacctccc aattttacc     540
accacacatt cgaaccaaaa ttttcacatc tataattttt atcgtcattt ttttattatt     600
tttttttttt attattatta aaaatgtttg gttttgaatt taaacacata aatcttgatt     660
tatgtgtttt tttttttttt ttttttttaa tttttaaaat ttaatttatt ttttattttt      720
tttttttatt tattttttaat tttttttaatt tttaattttt aaattttttat ttttaatttt     780
tttttttttt tttttttttt ttgaatcttc ccaagtttac ttgtatgcat tttaaatatt     840
taattaaatt agcccacaca caaaaataat tcttaaaaaaa aaaccctttt tttttttttt      900
tttttttttt ttctttccat tttaggttaa ataatttatt attatttttt tttttaataa     960
ttaaaaactt cctttatttt tttttctcta tcaataggaa atgacatctt cttcattaag    1020
taaaagtagt agtacaagta gtacaagtag caagaatgaa gaaaaaggtg aaaagaaaat    1080
ttatgattta atatcattag aagttccaag attacaagga ctttattaa gatcaacttt     1140
attttatgc gaaaaccatt atttaaagta agtattttta tttttttatta tttttttttt    1200
tttttatat gtgtggttag ttttttgatt ttttaaataa ttataaaaaa aaaaaaaata    1260
aaaaaaaac caattgtctt gtcactttca cacagtcaca cactcaatta ttttcgatta    1320
attgtaatct aatctttttt ttttttttttt tttaaattct aatttataa aaaaggaat     1380
tcattttat cgtcattata tacaaaaaat aaaatgccat taatttcaca atttaattta    1440
aatttatcac caacctttta tccaattgtt gatatttcaa atcatcaaca acaacaacaa    1500
aataaatctg aatttacatt taaaaaatat ttagcaactg atatgttgca tgataaagat    1560
ttaattaaat atcttcaaag taaaaattta gaaataaata gtcaatcatc atcatcatca    1620
tcatcaaata atcaatcatt aattaataat ataccagaga attcaattat aaattattat    1680
aatttatata tgactggaaa gataacacca aatgaaattg caatttttt tattgaatgt      1740
aaaaatcact ctgatgaaca atcaccacca ttgaaagcat ttataaagat attggaggat    1800
gatattaaat ctcaagcaat ggcaagtgct gaacgttgga atccggttc acctttgtca     1860
ttgattgatg gtgtaccaat ctcattaaaa gatgaaaatag accaaattgg atatcatacc    1920
acttgtggta caaccttttt ggagaaagta tttccaaatg ttaaaactga agattctggt    1980
gtagccaaaa tgttacgtca acaaggtgca attttagttg gaaagaataa tatgcacgaa    2040
attggtatct caacacttgg ttataatact cattttgggt tcactagaaa tccatataat    2100
ctcaatcatt atccaggtgg tagttcttca ggaagtgctt cttcagtatc ggctggttta    2160
aatccattaa gtattggttg tgatggtggt ggttcaatta gagtacctgc ttcattatgt    2220
ggtgtcgttg gttttaaaacc aacttttgca agagtttctc atggtggtat ttttgattta    2280
```

| | |
|---|---|
| tgttggtcag ttggtcatgt tggtccaatt ggttcgtcag taattgatac tgcaattggt | 2340 |
| tatgcttgta ttgctggttc tgactctgcc gatcatcaat ctgttttagc tgaacaatat | 2400 |
| ggcggtaaac caaccgttcc aatgtttact gaaattccat taattcaacc attaaaaggt | 2460 |
| ttaaaaattg gtgtttttta tgattggatt aatgattgta atatagaatt taaagattca | 2520 |
| acttatagta agtaaaaaaa aaaaaaaaa aaaacaatta aaaattaata ataatattaa | 2580 |
| taattcatta ctttgattaa ttattagaat gtattgaaat tttaaaagaa caaggagctg | 2640 |
| aaattataga aatagaaatt tcaaatttat tagtaactag attatcacaa ggcgcaatta | 2700 |
| ttttatcaga aatgaattca tctatgaaaa gagtaattat ttaatttatt taattatttt | 2760 |
| ttattaattt aattaaattt tattaatata atttttttt ttttttttt tttacattta | 2820 |
| aaaaaatagt ttaaaatta tagtaatgaa ttacaatatg atagtagaat ttcattatca | 2880 |
| attggtaata tattaccaac ttcagattat cttcaagcaa ataaagttag aactttttgt | 2940 |
| attgaacaat ttactgaaat ttttaaagga gttgatttaa ttgtaacacc aactaatgca | 3000 |
| atagctgcac ctgaaattga aaaaagtgtt ttgtctatgg gagaatcaaa ttttggatca | 3060 |
| gtaggtgaat taatgaaata tgttttatt ggaaatatta ctggtatccc tggcataact | 3120 |
| gttccagtgg gtctaacaaa agataaaaac ttaccaattg ttttcaaat tatggcaaag | 3180 |
| tggtggcaag aagatttact tttatacact tcttatgttt tagaaaaaaa tattgacttt | 3240 |
| aaaggaaaac cacaatatta taattgtcct ttaacaaatt gcacaaaccc aaataactaa | 3300 |
| tatttaaaat aaaataattt ataagatata ttttttttat tgtttattat tttttttttt | 3360 |
| taaaggtgag aattttaaaa tgtaaagaag ttattccttt taattttaat tttcaaataa | 3420 |
| ggaattttaa tttaaaaata aagtgtggct tttattttg tttataaata aattaaaaaa | 3480 |
| ataaatcagt tccaccaatt caattaataa attacaaagg agaaactatt tgtaagtatt | 3540 |
| gattctggaa taatatactt ttcaagttaa tttcttaatc atttgttttt tttcaatttc | 3600 |
| attttagaag actaggattt ttttttttt ataaataaac tattgtagta tacaattagt | 3660 |
| atgttatttt tatttattta ttttaggttt tttactttt gagaatttaa aatggtatgt | 3720 |
| tatttagat taggtaatta ataattaatt ggtggtgtaa ttgttggaat tagaggacta | 3780 |
| ggaatcgaac cttttttata tttttttat attttttta ctaggaatcg aacctacgat | 3840 |
| tttgcttttc tccccataaa aattcaccca ttgtgggtct cgatcccacg acctgcagct | 3900 |
| tagaaggctg ccgcaattcc aactttgcta aacgggcttt gatgaattct tgtaataaa | 3960 |
| gcttgttagc tttataaata tataggagat cgaaaaaaaa caaacaacaa caacaatctc | 4020 |
| tttttttgat tatttcattt ttcatataaa aaagacttaa aaaacaaata aataaataaa | 4080 |
| taaactatct taaaaagcca tcttttttact ttattgtaat ttattatttg tttcgttttg | 4140 |
| agaattttgc gtagcaaaat tttcaaaaaa aagcaaaaaa taatcagatc gaaaaaaaac | 4200 |
| aaacaacaac aacaatctct tttttgatt atttcatttt tcatataaaa aagacttaaa | 4260 |
| aaaaaaaaa aaaaaaaaa aaaaaaaaa aaaaaaaaa | 4300 |

<210> SEQ ID NO 5
<211> LENGTH: 41
<212> TYPE: DNA
<213> ORGANISM: artificial
<220> FEATURE:
<223> OTHER INFORMATION: Dd1 forward cloning primer

<400> SEQUENCE: 5
ctcgagaata gattaacaaa tatatcaaaa attagaaaat c        41

<210> SEQ ID NO 6
<211> LENGTH: 42
<212> TYPE: DNA
<213> ORGANISM: artificial
<220> FEATURE:
<223> OTHER INFORMATION: Dd1 reverse cloning primer

<400> SEQUENCE: 6
gtcgacttat tttaaataat ttggtgtaag tgatgtaaaa tc          42

<210> SEQ ID NO 7
<211> LENGTH: 27
<212> TYPE: DNA
<213> ORGANISM: artificial
<220> FEATURE:
<223> OTHER INFORMATION: dd1 forward expression primer

<400> SEQUENCE: 7
ctcgagaaat cattaataga tggaaaa                           27

<210> SEQ ID NO 8
<211> LENGTH: 27
<212> TYPE: DNA
<213> ORGANISM: artificial
<220> FEATURE:
<223> OTHER INFORMATION: dd1 reverse expression primer

<400> SEQUENCE: 8
gtcgacttat tttaaataat ttggtgt                           27

<210> SEQ ID NO 9
<211> LENGTH: 32
<212> TYPE: DNA
<213> ORGANISM: artificial
<220> FEATURE:
<223> OTHER INFORMATION: dd2 forward cloning primer

<400> SEQUENCE: 9
gtcgacttag ttatttgggt tgtgcaatt tg                      32

<210> SEQ ID NO 10
<211> LENGTH: 53
<212> TYPE: DNA
<213> ORGANISM: artificial
<220> FEATURE:
<223> OTHER INFORMATION: dd2 reverse cloning primer

<400> SEQUENCE: 10
catatgcacc accatcatca ccacacatct tcttcattaa gtaaagtag tag    53

<210> SEQ ID NO 11
<211> LENGTH: 44
<212> TYPE: DNA
<213> ORGANISM: artificial
<220> FEATURE:
<223> OTHER INFORMATION: dd1 overexpression primer forward

<400> SEQUENCE: 11
gaattcatga atagattaac aaatatatca aaaattagaa aatc         44

<210> SEQ ID NO 12
<211> LENGTH: 52
<212> TYPE: DNA
<213> ORGANISM: artificial
<220> FEATURE:

-continued

```
<223> OTHER INFORMATION: dd1 overexpression reverse primer

<400> SEQUENCE: 12
aagcttttag tgatgatggt gatgatgttt taaataattt ggtgtaagtg at        52

<210> SEQ ID NO 13
<211> LENGTH: 35
<212> TYPE: DNA
<213> ORGANISM: artificial
<220> FEATURE:
<223> OTHER INFORMATION: dd2 forward amplification primer

<400> SEQUENCE: 13
aagcttatga catcttcttc attaagtaaa agtag                            35

<210> SEQ ID NO 14
<211> LENGTH: 52
<212> TYPE: DNA
<213> ORGANISM: artificial
<220> FEATURE:
<223> OTHER INFORMATION: dd2 amplification reverse primer

<400> SEQUENCE: 14
aagcttttag tgatgatggt gatgatggtt atttgggttt gtgcaatttg tt        52
```